US010163163B1

(12) United States Patent
He et al.

(10) Patent No.: US 10,163,163 B1
(45) Date of Patent: Dec. 25, 2018

(54) SYSTEM AND METHOD TO ADJUST INSURANCE RATE BASED ON REAL-TIME DATA ABOUT POTENTIAL VEHICLE OPERATOR IMPAIRMENT

(71) Applicant: STATE FARM MUTUAL AUTOMOBILE INSURANCE COMPANY, Bloomington, IL (US)

(72) Inventors: Jibo He, Champaign, IL (US); Brian Mark Fields, Normal, IL (US); Steve Roberson, Normal, IL (US); Steve C. Cielocha, Bloomington, IL (US); Jufeng Peng, Normal, IL (US); Julian Coltea, Hinsdale, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 0 days.

(21) Appl. No.: 14/484,760

(22) Filed: Sep. 12, 2014

Related U.S. Application Data

(63) Continuation of application No. 13/717,514, filed on Dec. 17, 2012, now Pat. No. 8,930,269.

(51) Int. Cl.
    *G06Q 40/00* (2012.01)
    *G06Q 40/08* (2012.01)
    *B60K 28/06* (2006.01)

(52) U.S. Cl.
    CPC .............. *G06Q 40/08* (2013.01); *B60K 28/06* (2013.01)

(58) Field of Classification Search
    CPC ...................................................... G06Q 40/08
    USPC ........................................................... 705/4
    See application file for complete search history.

(56) References Cited

U.S. PATENT DOCUMENTS

| 5,311,877 | A | 5/1994 | Kishi |
| 5,465,079 | A | 11/1995 | Bouchard et al. |
| 5,585,785 | A | 12/1996 | Gwin et al. |
| 5,801,667 | A | 9/1998 | Shimizu et al. |
| 5,813,989 | A | 9/1998 | Saitoh et al. |

(Continued)

FOREIGN PATENT DOCUMENTS

| DE | 102007046037 B3 | 4/2009 |
| DE | 102011084552 A1 | 8/2012 |
| GB | 2465439 A | 5/2010 |

OTHER PUBLICATIONS

Office action for U.S. Appl. No. 13/717,506 dated May 22, 2013.

(Continued)

*Primary Examiner* — Jessica Lemieux
(74) *Attorney, Agent, or Firm* — Marshall, Gerstein & Borun LLP; Randall G. Rueth

(57) ABSTRACT

A method includes receiving data about potential impairment of a vehicle operator, wherein the data about potential impairment is generated by: (i) monitoring the vehicle operator with a first optical sensor, and (ii) monitoring an environment ahead of a vehicle operated by the vehicle operator with a second optical sensor. The computer-implemented method further includes assigning a plurality of scores based on the data about potential impairment, wherein each of the plurality of scores corresponds to a respective impairment indicator, and determining an impairment score for the vehicle operator by performing a mathematical operation on the plurality of scores, the impairment score summarizing a level of impairment of the vehicle operator.

20 Claims, 12 Drawing Sheets

(56) References Cited

U.S. PATENT DOCUMENTS

| | | | |
|---|---|---|---|
| 6,014,081 A | 1/2000 | Kojima et al. | |
| 6,091,334 A | 7/2000 | Galiana et al. | |
| 6,262,657 B1 | 7/2001 | Okuda et al. | |
| 6,313,749 B1 | 11/2001 | Horne et al. | |
| 6,346,887 B1 | 2/2002 | Van Orden et al. | |
| 6,661,345 B1 | 12/2003 | Bevan et al. | |
| 6,794,728 B1 | 9/2004 | Kithil | |
| 6,859,144 B2 | 2/2005 | Newman et al. | |
| 6,926,429 B2 | 8/2005 | Barlow et al. | |
| 6,927,694 B1 | 8/2005 | Smith et al. | |
| 6,989,754 B2 | 1/2006 | Kisacanin et al. | |
| 7,027,621 B1 | 4/2006 | Prokoski | |
| 7,054,723 B2 | 5/2006 | Seto et al. | |
| 7,138,922 B2 | 11/2006 | Strumolo et al. | |
| 7,202,792 B2 | 4/2007 | Zhang et al. | |
| 7,649,445 B2 | 1/2010 | Kuramori et al. | |
| 7,719,431 B2 | 5/2010 | Bolourchi | |
| 7,835,834 B2 | 11/2010 | Smith et al. | |
| 8,009,051 B2 | 8/2011 | Omi | |
| 8,311,858 B2 | 11/2012 | Everett et al. | |
| 9,117,242 B1 | 8/2015 | Ellis et al. | |
| 2001/0028309 A1 | 10/2001 | Torch | |
| 2004/0017106 A1 | 1/2004 | Aizawa et al. | |
| 2004/0059487 A1 | 3/2004 | Lich et al. | |
| 2004/0070509 A1 | 4/2004 | Grace et al. | |
| 2004/0090334 A1 | 5/2004 | Zhang et al. | |
| 2005/0030184 A1 | 2/2005 | Victor | |
| 2005/0073136 A1 | 4/2005 | Larsson et al. | |
| 2006/0053038 A1 | 3/2006 | Warren et al. | |
| 2007/0080816 A1 | 4/2007 | Haque et al. | |
| 2007/0132950 A1 | 6/2007 | Victor et al. | |
| 2007/0257804 A1 | 11/2007 | Gunderson et al. | |
| 2008/0160491 A1* | 7/2008 | Allen et al. | 434/362 |
| 2008/0255888 A1 | 10/2008 | Berkobin et al. | |
| 2008/0291008 A1 | 11/2008 | Jeon | |
| 2008/0319602 A1* | 12/2008 | McClellan et al. | 701/33 |
| 2009/0024419 A1 | 1/2009 | McClellan et al. | |
| 2009/0040054 A1 | 2/2009 | Wang et al. | |
| 2009/0109037 A1 | 4/2009 | Farmer | |
| 2009/0210257 A1 | 8/2009 | Chalfant et al. | |
| 2009/0243880 A1 | 10/2009 | Kiuchi | |
| 2010/0036290 A1 | 2/2010 | Noguchi et al. | |
| 2010/0131148 A1 | 5/2010 | Camhi et al. | |
| 2010/0131304 A1* | 5/2010 | Collopy et al. | 705/4 |
| 2010/0214087 A1 | 8/2010 | Nakagoshi et al. | |
| 2010/0245093 A1 | 9/2010 | Kobetski et al. | |
| 2011/0028309 A1 | 2/2011 | Hikazudani et al. | |
| 2011/0043350 A1 | 2/2011 | Ben David | |
| 2011/0206283 A1 | 8/2011 | Quarfordt et al. | |
| 2012/0002027 A1 | 1/2012 | Takahashi et al. | |
| 2012/0072244 A1 | 3/2012 | Collins et al. | |
| 2012/0089423 A1 | 4/2012 | Tamir et al. | |
| 2012/0092173 A1 | 4/2012 | Sanchez | |
| 2012/0135382 A1* | 5/2012 | Winston et al. | 434/65 |
| 2012/0158436 A1 | 6/2012 | Bauer et al. | |
| 2012/0169503 A1 | 7/2012 | Wu et al. | |
| 2012/0209634 A1 | 8/2012 | Ling et al. | |
| 2013/0038437 A1 | 2/2013 | Talati et al. | |
| 2013/0073114 A1 | 3/2013 | Nemat-Nasser et al. | |
| 2013/0144461 A1 | 6/2013 | Ricci | |
| 2013/0244210 A1 | 9/2013 | Nath et al. | |
| 2013/0302758 A1* | 11/2013 | Wright | 434/65 |
| 2014/0058761 A1 | 2/2014 | Freiberger et al. | |
| 2014/0167967 A1 | 6/2014 | He et al. | |

OTHER PUBLICATIONS

Final Office action for U.S. Appl. No. 13/717,506 dated Sep. 10, 2013.
Office action for U.S. Appl. No. 13/717,506 dated Jan. 21, 2014.
Office action for U.S. Appl. No. 13/908,114 dated Nov. 5, 2013.
Office Action in U.S. Appl. No. 13/908,114 dated Jun. 5, 2014.
Office Action for U.S. Appl. No. 13/717,514 dated May 24, 2013.
Office Action in U.S. Appl. No. 13/717,514 dated Oct. 24, 2013.
Fridstorm, Lasse, "A Framework for Assessing the Marginal External Accident Cost of Road Insurance Ratemaking", International Transport Forum Discussion Papers, Jul. 2011.
Love, Christopher M. "Cognitive Impairment and Dangerous Driving: A Decision-Making Model for the Psychologist to Balance Confidentiality with Safety"; Azusa Pacific University; May 2007.
Search Report in EP Application No. 13196067.6 dated Apr. 30, 2014.
Search Report in EP Application No. 13196072.6 dated May 6, 2014.
Notice of Allowance in U.S. Appl. No. 13/717,506 dated Nov. 13, 2014.
Office Action in U.S. Appl. No. 13/908,114 dated Oct. 23, 2014.
Office Action for U.S. Appl. No. 14/484,719 dated Dec. 5, 2014.
Office Action for U.S. Appl. No. 14/503,717 dated Dec. 26, 2014.
Angkititrakul et al., "An Improved Driver-Behavior Model with Combined Individual and General Driving Characteristics", 2012 Intelligent Vehicles Symposium, Spain, Jun. 3-7, 2012, pp. 426,431.
Office Action in U.S. Appl. No. 14/484,719 dated Apr. 16, 2015.
Office Action in U.S. Appl. No. 13/908,114 dated May 21, 2015.
Notice of Allowance in U.S. Appl. No. 14/484,922 dated Jun. 15, 2015.
Office Action for U.S. Appl. No. 14/484,922 dated Jan. 14, 2015.
Office Action in U.S. Appl. No. 14/503,717 dated Jun. 23, 2015.
Office Action in U.S. Appl. No. 14/797,427 dated Dec. 4, 2015.
Office Action in U.S. Appl. No. 14/503,717 dated Jan. 22, 2016.
Office Action in U.S. Appl. No. 14/484,719 dated Feb. 3, 2016.
Office Action in U.S. Appl. No. 14/804,610 dated Oct. 16, 2015.
Office Action in U.S. Appl. No. 14/797,409 dated Nov. 12, 2015.
Office Action in U.S. Appl. No. 14/484,719 dated Jul. 28, 2015.
Office Action in U.S. Appl. No. 14/797,427 dated Apr. 1, 2016.
Office Action in U.S. Appl. No. 14/804,610 dated Aug. 26, 2016.
Office Action in U.S. Appl. No. 14/484,719 dated Sep. 22, 2016.
Office Action in U.S. Appl. No. 14/503,717 dated May 12, 2016.
Office Action in U.S. Appl. No. 14/797,409 dated Jun. 3, 2016.
Office Action in U.S. Appl. No. 14/804,610 dated Jan. 13, 2017.
Office Action for U.S. Appl. No. 14/797,427 dated Feb. 9, 2017.
Office Action in U.S. Appl. No. 14/484,719 dated Mar. 24, 2017.
Office Action for U.S. Appl. No. 14/804,610 dated Dec. 12, 2017.
Office Action for U.S. Appl. No. 14/484,719 dated Dec. 28, 2017.
Office Action in U.S. Appl. No. 14/804,610 dated Jun. 19, 2017.
Office Action in U.S. Appl. No. 14/978,416 dated Jun. 30, 2017.
Office Action in U.S. Appl. No. 14/797,427 dated Jul. 7, 2017.
Office Action in U.S. Appl. No. 14/503,717 dated Jul. 7, 2017.
Office Action in U.S. Appl. No. 15/481,651 dated Jul. 13, 2017.
Office Action for U.S. Appl. No. 14/484,719 dated Jul. 27, 2017.
Office Action in U.S. Appl. No. 14/797,427 dated Nov. 1, 2017.
Office Action in U.S. Appl. No. 14/503,717 dated Nov. 13, 2017.
Office Action in U.S. Appl. No. 14/797,427 dated May 14, 2018.
Office Action in U.S. Appl. No. 14/804,610 dated Feb. 29, 2016.

* cited by examiner

SYSTEM AND METHOD TO ADJUST INSURANCE RATE BASED ON REAL-TIME DATA ABOUT POTENTIAL VEHICLE OPERATOR IMPAIRMENT

RELATED APPLICATIONS

This application is a continuation application of U.S. application Ser. No. 13/717,514, filed Dec. 17, 2012, the disclosure of which is hereby incorporated herein by reference in its entirety for all purposes.

TECHNICAL FIELD

The present disclosure generally relates to a system and a method for adjusting an insurance rate based on real-time data about whether a vehicle operator is impaired and, more particularly, to a computer system to analyze the real-time data to adjust a property and casualty insurance rate.

BACKGROUND

Every year many vehicle accidents are caused by impaired driving. One common kind of impaired driving is drowsy driving. If the vehicle operator falls asleep for even a second while driving, the results can be disastrous. Another common kind of impaired driving is distracted driving. Modern vehicles come equipped with any number of distractions including stereos, air-conditioners, navigation systems, etc. Furthermore, a vehicle operator can be distracted by another passenger or by articles the vehicle operator brings into the vehicle (e.g., a mobile telephone, book, etc.).

SUMMARY

In one embodiment, a computer-implemented method comprises receiving, via a computer network, data about potential impairment of a vehicle operator, wherein the data about potential impairment is generated by: (i) monitoring the vehicle operator with a first optical sensor, and (ii) monitoring an environment ahead of a vehicle operated by the vehicle operator with a second optical sensor. The computer-implemented method further includes assigning, by one or more processors, a plurality of scores based on the data about potential impairment, wherein each of the plurality of scores corresponds to a respective impairment indicator, and determining, by the one or more processors, an impairment score for the vehicle operator by performing a mathematical operation on the plurality of scores, the impairment score summarizing a level of impairment of the vehicle operator.

In another embodiment, a computer device comprises one or more processors and a non-transitory program memory. The non-transitory memory stores computer-executable instructions that, when executed by the one or more processors, cause the computer device to receive, via a computer network, data about potential impairment of a vehicle operator, wherein the data about potential impairment is generated by: (i) monitoring the vehicle operator with a first optical sensor, and (ii) monitoring an environment ahead of a vehicle operated by the vehicle operator with a second optical sensor. Further, the instructions cause the computer device to assign a plurality of scores based on the data about potential impairment, wherein each of the plurality of scores corresponds to a respective impairment indicator, and determine an impairment score for the vehicle operator by performing a mathematical operation on the plurality of scores, the impairment score summarizing a level of impairment of the vehicle operator.

In yet another embodiment, a non-transitory, computer-readable medium stores instructions that, when executed by one or more processors of a computer system, cause the computer system to receive, via a computer network, data about potential impairment of a vehicle operator, wherein the data about potential impairment is generated by: (i) monitoring the vehicle operator with a first optical sensor, and (ii) monitoring an environment ahead of a vehicle operated by the vehicle operator with a second optical sensor. The instructions further cause the computer system to assign a plurality of scores based on the data about potential impairment, wherein each of the plurality of scores corresponds to a respective impairment indicator, and determine an impairment score for the vehicle operator by performing a mathematical operation on the plurality of scores, the impairment score summarizing a level of impairment of the vehicle operator.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

As used herein, the term "impairment" refers to any of a number of conditions that may reduce vehicle operator performance. A vehicle operator may be impaired if the vehicle operator is drowsy, asleep, distracted, intoxicated, ill, injured, suffering from a sudden onset of a medical condition, etc. Additionally, as used herein, the term "vehicle" may refer to any of a number of motorized transportation devices. A vehicle may be a car, truck, bus, train, boat, plane, etc.

Figure 1:
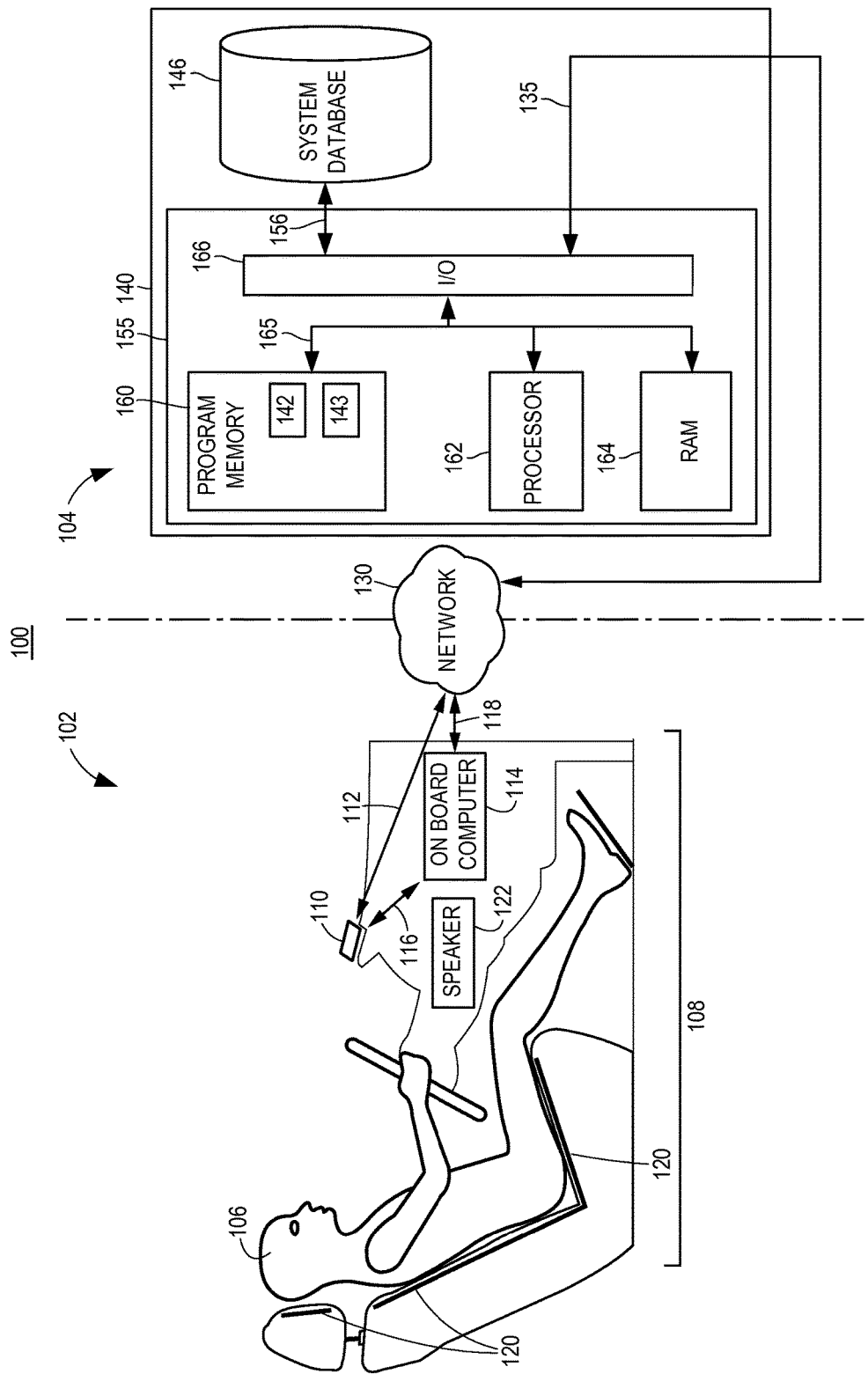
FIG. 1 illustrates a block diagram of a computer network, a computer server, a mobile device, and an on-board computer on which an exemplary vehicle operator impairment monitoring system and method may operate in accordance with the described embodiments.

FIG. 1 illustrates a block diagram of an exemplary vehicle operator impairment monitoring system 100. The high-level architecture includes both hardware and software applications, as well as various data communications channels for communicating data between the various hardware and software components. The vehicle operator impairment monitoring system 100 may be roughly divided into front-end components 102 and back-end components 104. The front-end components 102 are disposed within one or more mobile devices 110. The mobile device 110 may be permanently or removably installed in a vehicle 108 (e.g., a car, truck, etc.). Additionally or alternatively, the vehicle 108 may include an on-board computer 114. The on-board computer 114 may be permanently installed in a vehicle 108 and may interface with various sensors in the vehicle 108 (e.g., a braking sensor, a speedometer, a tachometer, etc.) and/or may interface with various external output devices in the vehicle 108 such as one or more tactile alert systems 120, one or more speakers 122, one or more displays (not shown), etc. The on-board computer 114 may supplement the functions performed by the mobile device 110 described herein by, for example, sending and/or receiving information to and from the mobile device 110. Alternatively, the on-board computer 114 may perform all of the functions of the mobile device 110 described herein. In such cases, no mobile device 110 may be present in the system 100. One or more vehicle operators 106 may be operating the vehicle 108. The mobile device 110 and on-board computer 114 may communicate with the network 130 over links 112 and 118, respectively. Additionally, the mobile device 110 and on-board computer 114 may communicate with one another directly over link 116. The vehicle 108 may also include a tactile alert system 120 (e.g., a seat that can vibrate) that may present tactile alerts to the vehicle operator 106 on command from the mobile device 110 and/or the on-board computer 114 as discussed herein. While shown in a slightly reclined sitting position, those of ordinary skill in the art will appreciate that the vehicle operator 106 could be situated in any number of ways (e.g., reclining at a different angle, standing, etc.) and operating the vehicle using controls other than the steering wheel and pedals shown in FIG. 1 (e.g., one or more sticks, yokes, levers, etc.). The plurality of mobile devices 110 may be located, by way of example rather than limitation, in separate geographic locations from each other, including different areas of the same city, different cities, or different states, and being in mobile vehicles, may move from one geographic location to another.

The front-end components 102 communicate with the back-end components 104 via the network 130. The network 130 may be a proprietary network, a secure public internet, a virtual private network or some other type of network, such as dedicated access lines, plain ordinary telephone lines, satellite links, combinations of these, etc. Where the network 130 comprises the Internet, data communications may take place over the network 130 via an Internet communication protocol. The back-end components 104 include a server 140. The server 140 may include one or more computer processors adapted and configured to execute various software applications and components of the vehicle operator impairment monitoring system 100, in addition to other software applications. The server 140 further includes a database 146. The database 146 is adapted to store data related to the operation of the vehicle operator impairment monitoring system 100. Such data might include, for example, data collected by a mobile device 110 and/or on-board computer 114 pertaining to the vehicle operator impairment monitoring system 100 and uploaded to the server 140 such as images, sensor inputs, data analyzed according to the methods discussed below, or other kinds of data. The server 140 may access data stored in the database 146 when executing various functions and tasks associated with the operation of the vehicle operator impairment monitoring system 100.

Although the vehicle operator impairment monitoring system 100 is shown to include one server 140, one mobile device 110, and one on-board computer 114 it should be understood that different numbers of servers 140, devices 110, and on-board computers 114 may be utilized. For example, the system 100 may include a plurality of servers 140 and hundreds of devices 110, all of which may be interconnected via the network 130. As discussed above, the mobile device 110 may perform the various functions described herein in conjunction with the on-board computer 114 or alone (in such cases, the on-board computer 114 need not be present). Likewise, the on-board computer 114 may perform the various functions described herein in conjunction with the mobile device 110 or alone (in such cases, the mobile device 110 need not be present). Furthermore, the processing performed by the one or more servers 140 may be distributed among a plurality of servers 140 in an arrangement known as "cloud computing." According to the disclosed example, this configuration may provide several advantages, such as, for example, enabling near real-time uploads and downloads of information as well as periodic uploads and downloads of information. This may provide for a thin-client embodiment of the mobile device 110 and/or on-board computer 114 discussed herein as well as a primary backup of some or all of the data gathered by the mobile device 110 and/or on-board computer 114. Alternatively, the vehicle operator impairment monitoring system 100 may include only the front-end components 102. For example, a mobile device 110 and/or on-board computer 114 may perform all of the processing associated with gathering data, determining whether the vehicle operator 106 is impaired, alerting the vehicle operator 106 (e.g., visually, audibly, tactilely), and/or providing suggestions on how to decrease impaired vehicle operation as described below. As such, the vehicle operator impairment monitoring system 100 may be a "stand-alone" system, neither sending nor receiving information over the network 130.

The server 140 may have a controller 155 that is operatively connected to the database 146 via a link 156. It should be noted that, while not shown, additional databases may be linked to the controller 155 in a known manner. The controller 155 may include a program memory 160, a processor 162 (may be called a microcontroller or a microprocessor), a random-access memory (RAM) 164, and an input/output (I/O) circuit 166, all of which may be interconnected via an address/data bus 165. The program memory 160 may be configured to store computer-readable instructions that when executed by the processor 162 cause the server 140 to implement a server application 142 and a web server 143. The instructions for the server application 142 may cause the server 140 to implement the methods described herein. While shown as a single block in FIG. 1, it will be appreciated that the server application 142 may include a number of different programs, modules, routines, and sub-routines that may collectively cause the server 140 implement the server application 142. It should be appreciated that although only one microprocessor 162 is shown, the controller 155 may include multiple microprocessors 162. Similarly, the memory of the controller 155 may include multiple RAMs 164 and multiple program memories 160. Further, while the instructions for the server application 142 and web server 143 are shown being stored in the program memory 160, the instructions may additionally or alternatively be stored in the database 146 and/or RAM 164. Although the I/O circuit 166 is shown as a single block, it should be appreciated that the I/O circuit 166 may include a number of different types of I/O circuits. The RAM(s) 164 and program memories 160 may be implemented as semiconductor memories, magnetically readable memories, and/or optically readable memories, for example. The controller 155 may also be operatively connected to the network 130 via a link 135.

Figure 2:
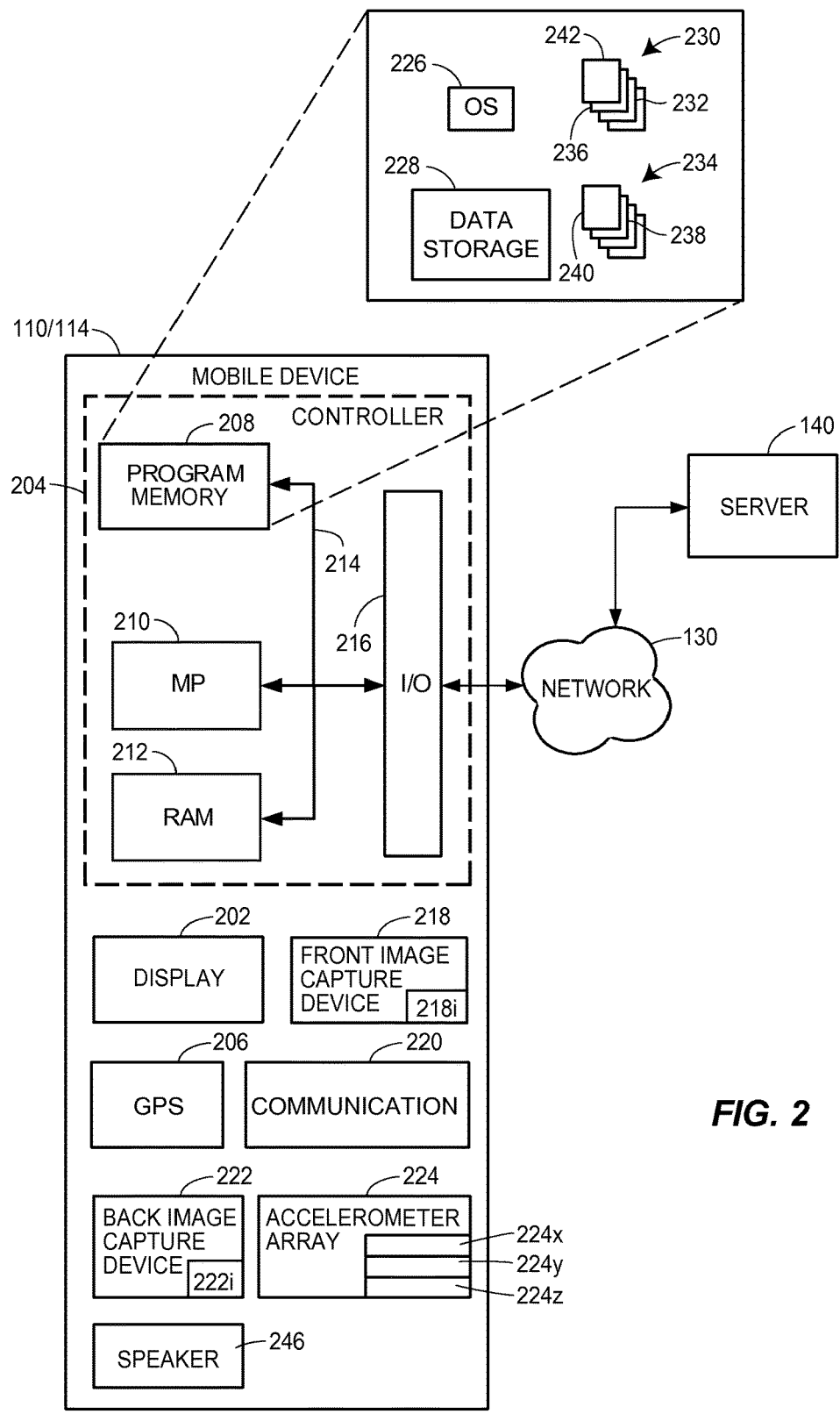
FIG. 2 illustrates a block diagram of an exemplary mobile device.

Referring now to FIG. 2, the mobile device 110 may include a display 202, a Global Positioning System (GPS) unit 206, a communication unit 220, a front image capture device 218, a back image capture device 222, an accelerometer array 224, a user-input device (not shown), a speaker 246, and, like the server 140, a controller 204. Similarly, the on-board computer 114 may comprise a display 202, a Global Positioning System (GPS) unit 206, a communication unit 220, a front image capture device 218, a back image capture device 222, an accelerometer array 224, a user-input device (not shown), a speaker 246, and, like the mobile device 110, a controller 204. The mobile device 110 and on-board computer 114 may be integrated into a single device or one can perform the functions of both. It will be appreciated that functions performed by either the mobile device 110 or the on-board computer 114 may also be performed by the on-board computer 114 in concert with the mobile device 110. The mobile device 110 may be either a general-use mobile personal computer, cellular phone, smart phone, tablet computer, other wearable computer (e.g., a watch, glasses, etc.), or a dedicated vehicle impairment monitoring computer. The on-board computer 114 may be a general-use on-board computer capable of performing many functions relating to vehicle operation or a dedicated vehicle impairment monitoring computer. Further, the on-board computer 114 may be installed by the manufacturer of the vehicle 108 or as an aftermarket modification to the vehicle 108. Further, the mobile device 110 and/or on-board computer 114 may be a thin-client device which outsources some or most processing to the server 140.

Similar to the controller 155, the controller 204 includes a program memory 208, one or more microcontroller or a microprocessor (MP) 210, a random-access memory (RAM) 212, and an input/output (I/O) circuit 216, all of which are interconnected via an address/data bus 214. The program memory 208 includes an operating system 226, a data storage 228, a plurality of software applications 230, and a plurality of software routines 234. The operating system 226, for example, may include one of a plurality of mobile platforms such as the iOS®, Android™ Palm® webOS, Windows® Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. The data storage 228 may include data such as user profiles and preferences, application data for the plurality of applications 230, routine data for the plurality of routines 234, and other data necessary to interact with the server 140 through the digital network 130. In some embodiments, the controller 204 may also include, or otherwise be communicatively connected to, other data storage mechanisms (e.g., one or more hard disk drives, optical storage drives, solid state storage devices, etc.) that reside within the mobile device 110 and/or on-board computer 114.

The GPS unit 206 may use "Assisted GPS" (A-GPS), satellite GPS, or any other suitable global positioning protocol (e.g., the GLONASS system operated by the Russian government) or system that locates the position the mobile device 110 and/or on-board computer 114. For example, A-GPS utilizes terrestrial cell phone towers or Wi-Fi hotspots (e.g., wireless router points) to more accurately and more quickly determine location of the mobile device 110 and/or on-board computer 114 while satellite GPS generally are more useful in more remote regions that lack cell towers or Wi-Fi hotspots. The front and back image capture devices 218 and 222 may be built-in cameras within the mobile device 110 and/or on-board computer 114 and/or may be peripheral cameras, such as webcams, cameras installed inside the vehicle 108, cameras installed outside the vehicle 108, etc., that are communicatively coupled with the mobile device 110 and/or on-board computer 114. The front image capture device 218 may be oriented toward the vehicle operator 106 to observe the vehicle operator 106 as described below. The back image capture device 222 may be oriented toward the front of the vehicle 108 to observe the road, lane markings, and/or other objects in front of the vehicle 108. Some embodiments may have both a front image capture device 218 and a back image capture device 222, but other embodiments may have only one or the other. Further, either or both of the front image capture device 218 and back image capture device 222 may include an infrared illuminator 218$i$, 222$i$, respectively, to facilitate low light and/or night image capturing. Such an infrared illuminator 218$i$, 222$i$ may be automatically activated when light is insufficient for image capturing. The accelerometer array 224 may be one or more accelerometers positioned to determine the force and direction of movements of the mobile device 110 and/or on-board computer 114. In some embodiments, the accelerometer array 224 may include an X-axis accelerometer 224$x$, a Y-axis accelerometer 224$y$, and a Z-axis accelerometer 224$z$ to measure the force and direction of movement in each dimension respectively. It will be appreciated by those of ordinary skill in the art that a three dimensional vector describing a movement of the mobile device 110 and/or on-board computer 114 through three dimensional space can be established by combining the outputs of the X-axis, Y-axis, and Z-axis accelerometers 224$x, y, z$ using known methods. The GPS unit 206, the front image capture device 218, the back image capture device 222, and accelerometer array 224 may be referred to collectively as the "sensors" of the mobile device 110 and/or on-board computer 114. Of course, it will be appreciated that additional GPS units 206, front image capture devices 218, back image capture devices 222, and/or accelerometer arrays 224 may be added to the mobile device 110 and/or on-board computer 114. Further, the mobile device 110 and/or on-board computer 114 may also include (or be coupled to) other sensors such as a thermometer, microphone, thermal image capture device, electroencephalograph (EEG), galvanic skin response (GSR) sensor, alcohol sensor, other biometric sensors, etc. A thermometer and/or thermal image capture device may be used to determine an abnormal vehicle operator 106 body temperature or a change in the vehicle operator's 106 body temperature (e.g., a decrease in body temperature may indicate that the vehicle operator 106 is drowsy or falling asleep, an elevated body temperature may indicate that the vehicle operator is ill). A microphone may be used to receive voice inputs as described below, and may also be used to detect irregularities in the voice of the vehicle operator 106 indicating that vehicle operator 106 is under stress. An EEG may be used to determine whether a vehicle operator 106 is drowsy (i.e., the EEG shows that brain activity has decreased or matches known brain activity patterns associated with drowsiness), stressed, distracted, or otherwise impaired. A GSR sensor may be used to detect whether the vehicle operator 106 is stressed (i.e., that the conductance of the vehicle operator's 106 skin has varied from its normal level). An alcohol sensor may detect whether there is alcohol in the vehicle operator's 106 breath and/or in the air inside the vehicle 108, which may indicate that the vehicle operator 106 is intoxicated.

The communication unit 220 may communicate with the server 140 via any suitable wireless communication protocol network, such as a wireless telephony network (e.g., GSM, CDMA, LTE, etc.), a Wi-Fi network (802.11 standards), a WiMAX network, a Bluetooth network, etc. The communication unit 220 may also be capable of communicating using a near field communication standard (e.g., ISO/IEC 18092, standards provided by the NFC Forum, etc.). Further, the communication unit 220 may use a wired connection to the server 140.

The user-input device (not shown) may include a "soft" keyboard that is displayed on the display 202 of the mobile device 110 and/or on-board computer 114, an external hardware keyboard communicating via a wired or a wireless connection (e.g., a Bluetooth keyboard), an external mouse, or any other suitable user-input device. The user-input device (not shown) may also include a microphone capable of receiving user voice input. As discussed with reference to the controllers 155 and 224, it should be appreciated that although FIG. 2 depicts only one microprocessor 210, the controller 204 may include multiple microprocessors 210. Similarly, the memory of the controller 204 may include multiple RAMs 212 and multiple program memories 208. Although the FIG. 2 depicts the I/O circuit 216 as a single block, the I/O circuit 216 may include a number of different types of I/O circuits. The controller 204 may implement the RAM(s) 212 and the program memories 208 as semiconductor memories, magnetically readable memories, and/or optically readable memories, for example.

The one or more processors 210 may be adapted and configured to execute any of one or more of the plurality of software applications 230 and/or any one or more of the plurality of software routines 234 residing in the program memory 208, in addition to other software applications. One of the plurality of applications 230 may be a client application 232 that may be implemented as a series of machine-readable instructions for performing the various tasks associated with implementing the vehicle operator impairment monitoring system 100 as well as receiving information at, displaying information on, and transmitting information from the mobile device 110 and/or on-board computer 114. The client application 232 may function to implement a stand-alone system or as a system wherein the front-end components 102 communicate with back-end components 104 as described herein. The client application 232 may include machine-readable instruction for implementing a user interface to allow a user to input commands to and receive information from vehicle operator impairment monitoring system 100. One of the plurality of applications 230 may be a native web browser 236, such as Apple's Safari®, Google Android™ mobile web browser, Microsoft Internet Explorer® for Mobile, Opera Mobile™, that may be implemented as a series of machine-readable instructions for receiving, interpreting, and displaying web page information from the server 140 or other back-end components 104 while also receiving inputs from the user. Another application of the plurality of applications may include an embedded web browser 242 that may be implemented as a series of machine-readable instructions for receiving, interpreting, and displaying web page information from the servers 140 or other back-end components 104 within the client application 232. One of the plurality of routines may include an image capture routine 238 that coordinates with the image capture devices 218, 222 to retrieve image data for use with one or more of the plurality of applications, such as the client application 232, or for use with other routines. Another routine in the plurality of routines may include an accelerometer routine 240 that determines the force and direction of movements of the mobile device 110 and/or on-board computer 114. The accelerometer routine 240 may process data from the accelerometer array 224 to determine a vector describing the motion of the mobile device 110 and/or on-board computer 114 for use with the client application 232. In some embodiments where the accelerometer array 224 has X-axis, Y-axis, and Z-axis accelerometers 224$x,y,z$, the accelerometer routine 240 may combine the data from each accelerometer 224$x,y,z$ to establish a vector describing the motion of the mobile device 110 and/or on-board computer 114 through three dimensional space. Furthermore, in some embodiments, the accelerometer routine 240 may use data pertaining to less than three axes, such as when determining when the vehicle 108 is braking.

A user may launch the client application 232 from the mobile device 110 and/or on-board computer 114, to access the server 140 to implement the vehicle operator impairment monitoring system 100. Additionally, the customer or the user may also launch or instantiate any other suitable user interface application (e.g., the native web browser 236, or any other one of the plurality of software applications 230) to access the server 140 to realize the vehicle operator impairment monitoring system 100.

The server 140 may further include a number of software applications. The various software applications are responsible for generating the data content to be included in the web pages sent from the web server 143 to the mobile device 110 and/or on-board computer 114. The software applications may be executed on the same computer processor as the web server application 143, or on different computer processors.

In embodiments where the mobile device 110 and/or on-board computer 114 is a thin-client device, the server 140 may perform many of the processing functions remotely that would otherwise be performed by the mobile device 110 and/or on-board computer 114. In such embodiments, the mobile device 110 and/or on-board computer 114 may gather data from its sensors as described herein, but instead of analyzing the data locally, the mobile device 110 and/or on-board computer 114 may send the data to the server 140 for remote processing. The server 140 may perform the analysis of the gathered data to determine whether the vehicle operator 106 may be impaired as described below. If the server 140 determines that the vehicle operator 106 may be impaired, the server 140 may command the mobile device 110 and/or on-board computer 114 to alert the vehicle operator as described below. Additionally, the server 140 may generate the metrics and suggestions described below based on the gathered data.

Figure 3:
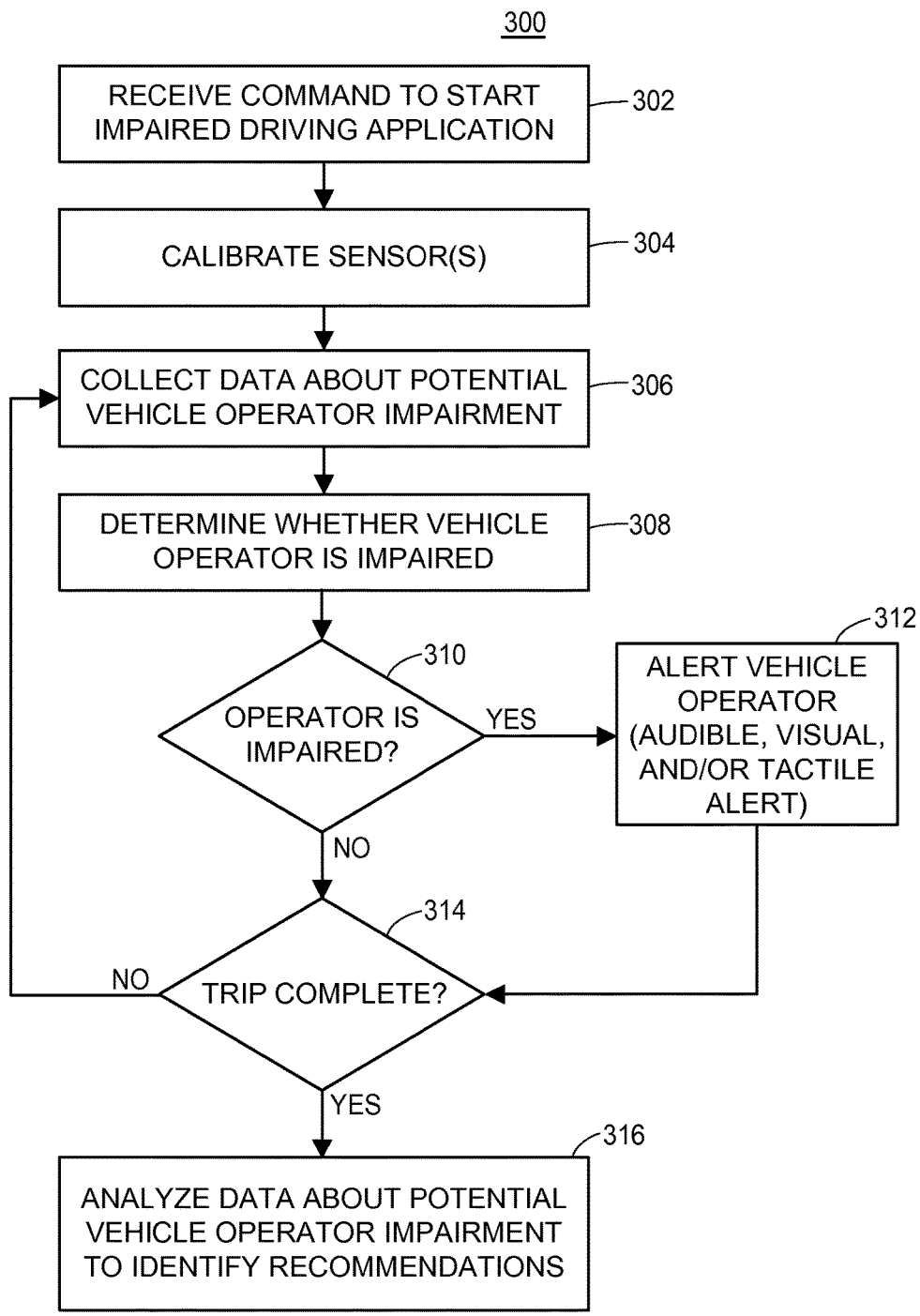
FIG. 3 depicts an exemplary vehicle operator impairment monitoring method for implementing the vehicle operator impairment monitoring system in accordance with the presently described embodiments.

FIG. 3 is a flow diagram depicting an exemplary embodiment of a vehicle operator impairment monitoring method 300 implemented by the vehicle operator impairment monitoring system 100. More particularly the method 300 may be performed by the mobile device 110 and/or on-board computer 114 and/or the mobile device 110 and/or on-board computer 114 in conjunction with the server 140. The method 300 may be initiated by a command (block 302). The command may be a user command received by the mobile device 110 and/or on-board computer 114 via the client application 232. Alternatively or additionally, the command may be sent by the server 140 or may be generated automatically by the mobile device 110 and/or on-board computer 114 after the meeting of a condition (e.g., the vehicle 108 has been started; the mobile device 110 is within a specified distance from the vehicle, a certain time, etc.). Next, the sensors of the mobile device 110 and/or on-board computer 114 may be calibrated (block 304). For example the front image capture device 218 may attempt to detect the face and eye(s) of the vehicle operator 106. Calibration may further entail adjusting the front image capture device 218 to account for the vehicle operator's 106 skin tone, facial characteristics, etc., ambient light in the vehicle, the background behind the vehicle operator 106, etc. The back image capture device 222 may also be calibrated, such as, to attempt to detect the road in front of the vehicle, identify lane markings, and identify other vehicles on the road. Calibration may further entail adjusting the back image capture device 222 to account for the color of the road, road conditions (e.g., a wet road from rain or an icy road from snow), the color of lane markings, the time of day and ambient light, etc. In some embodiments the accelerometer array 224 may also be calibrated. Such calibration may entail accounting for constant vibration (e.g., the vibration caused by the engine of the vehicle 108) or other repetitive forces applied to the mobile device 110 and/or on-board computer 114.

Figure 4:
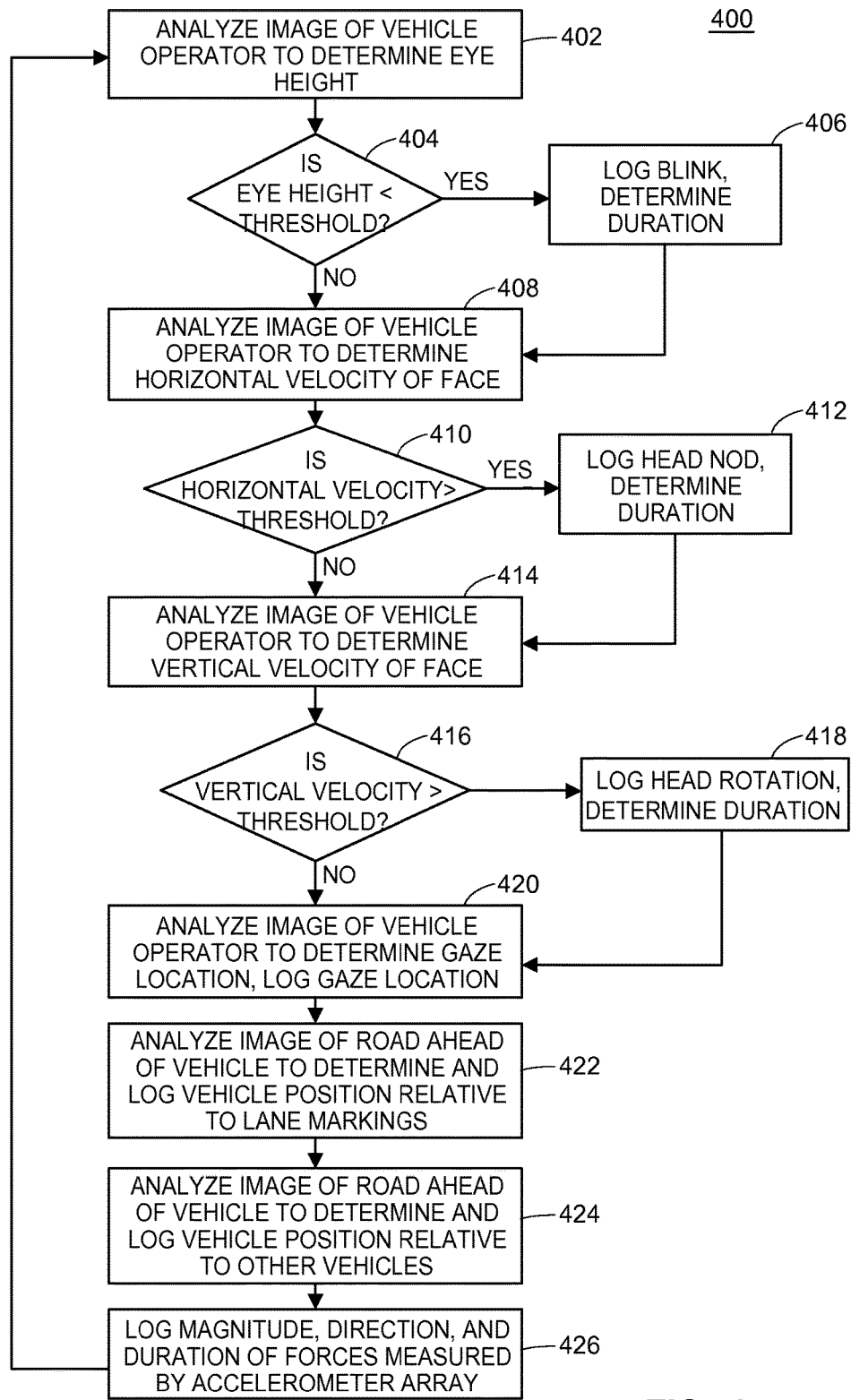
FIG. 4 depicts an exemplary primary indicator logging method for implementing the vehicle operator impairment monitoring system in accordance with the presently described embodiments.

After calibration, the mobile device 110 and/or on-board computer 114 may begin to collect data about potential vehicle operator impairment using the sensor(s) on the mobile device 110 and/or on-board computer 114 (block 306). FIG. 4 is a flow diagram depicting an exemplary embodiment of a primary impairment indicator logging method 400 implemented by the vehicle operator impairment monitoring system 100 while gathering data about potential vehicle operator impairment at block 306. Impairment indicators may be a series of measurements of conditions or characteristics pertaining to potential vehicle operator impairment. Accordingly, the front image capture device 218, back image capture device 222, and accelerometer array 224, may be used to measure these conditions and characteristics. Such measurements may be logged periodically (e.g., every millisecond, every second, etc.) or may be logged conditionally on the occurrence of an event (e.g., an eye blink of a vehicle operator 106) and stored in data storage 228 as an impairment indicator log. Such impairment indicator logs may also include a timestamp to note the time of the measurement. The vehicle operator impairment monitoring system 100 may make impairment indicator logs for primary impairment indicators such as: vehicle operator blinks, vehicle operator head nods, vehicle operator head rotations, vehicle operator gaze location, vehicle position relative to lane markings, vehicle position relative to other vehicles; and acceleration along the X, Y, or Z axes. The vehicle operator impairment monitoring system 100 may derive secondary impairment indicators from the primary impairment indicators such as: frequency of vehicle operator blinks, duration of vehicle operator blinks, percent eye closed (PERCLOS), vehicle operator gaze fixation, lane deviation, failure to maintain lane centering, time to collision, time to brake, time to react, longitudinal vehicle control, vehicle braking, vehicle acceleration, and lateral acceleration. Both the impairment indicator logs and secondary impairment may be logged separately (e.g., a log for blinks, a log for head rotations, etc.) or may be logged together. These separate or integrated logs may be stored in data storage 228 or may be transmitted to the server 140 via the network 130 for remote storage.

When logging vehicle operator blinks, the mobile device 110 and/or on-board computer 114 may use the front image capture device 218 to watch the eye or eyes of the vehicle operator 106 (block 402) and determine when the visible size of the eye or eyes goes below a threshold value (block 404) and when the visible size of the eye or eyes has increased above the threshold value after a blink is logged (block 406). For example, the front image capture device 218 may watch the eye of the vehicle operator 106 to determine when the opening of the eye shrinks below a threshold level (e.g., two pixels) indicating that the eye is closed or nearly closed. The eye opening threshold level may be set during calibration at block 304 and/or configured by a sensitivity setting (i.e., a higher threshold value is less sensitive than a lower threshold value). The mobile device 110 and/or on-board computer 114 may create a primary impairment indicator log for this blink with a timestamp (block 406). Additionally, the front image capture device 218 may watch the eye of the vehicle operator 106 after a blink to determine when the opening of the eye grows above a threshold level (e.g., two pixels) indicating that the eye is opening after being closed (block 406). Operator head nods may be measured by monitoring the face of the vehicle operator 106 with the front image capture device 218 (block 408) and detecting a vertical acceleration of the vehicle operator's 106 face exceeding a threshold value (block 410). The vertical acceleration threshold level may be set during calibration at block 304 and/or configured by a sensitivity setting (i.e., a higher threshold value is less sensitive than a lower threshold value). If the vertical acceleration of the face exceeds the threshold value, the client application 232 may create a primary impairment indicator log for this head nod with a timestamp (block 412). Additionally, head nod duration may be calculated from when a head nod begins until the head of the vehicle operator 106 returns to the normal position (i.e., looking ahead). Similarly, operator head rotations may be measured by monitoring the face of the vehicle operator 106 with the front image capture device 218 (block 414) and detecting a horizontal acceleration the vehicle operator's 106 face exceeding a threshold value (block 416). The horizontal acceleration threshold level may be set during calibration at block 304 and/or configured by a sensitivity setting (i.e., a higher threshold value is less sensitive than a lower threshold value). If the horizontal acceleration of the face exceeds the threshold value, the client application 232 may create a primary impairment indicator log for this head rotation with a timestamp (block 418). Additionally, head rotation duration may be calculated from when a head rotation begins until the head of the vehicle operator 106 returns to the normal position (i.e., looking ahead). Vehicle operator gaze location may be determined by monitoring the eye or eyes of vehicle operator 106 with the front image capture device 218 (block 420). Vehicle operator gaze location may be used to determine when the vehicle operator 106 is looking at the road, mirrors, the dashboard, stereo or air conditioning controls, a mobile device, etc. In some embodiments, the client application 232 may log whether the vehicle operator 106 is looking at a distraction (e.g., the stereo) or in the direction of an important area for vehicle operation (e.g., the road, mirrors, etc.). The vehicle operator impairment monitoring system 100 may differentiate between the important areas for vehicle operation in gaze location logs. The vehicle operator impairment monitoring system 100 may include a first value in the gaze location log indicating that the vehicle operator was looking at the road, a second value in the gaze location log indicating that the vehicle operator was looking at the rear view mirror, a third value in the gaze location log indicating that the vehicle operator was looking at the left side mirror, a fourth value in the gaze location log indicating that the vehicle operator was looking at the right side mirror, and a fifth value in the gaze location log indicating that the vehicle was looking at the dashboard gauges (e.g., speedometer). The client application 232 may also include a timestamp in the gaze location log. If a gaze location log is made every time the vehicle operator starts looking at a different object, then the duration of a particular vehicle operator gaze can be determined by the difference between the time the vehicle operator 106 began looking at the object and the time the vehicle operator 106 begins looking at another object.

The back image capture device 222 may be used to monitor conditions on the road including identifying lane markings and/or other vehicles on the road. Vehicle position relative to lane markings may be determined by processing an image or series of images captured by the back image capture device 222 to determine the distance of the vehicle 108 from lane markings on either or both sides of the vehicle 108 (block 422). The mobile device 110 and/or on-board computer 114 may determine vehicle position relative to lane markings regularly with a timestamp and store the log of vehicle position relative to lane markings in data storage 228 or send the log of vehicle position relative to lane markings to the server 140 for remote storage. Similarly, vehicle position relative to other vehicles (also referred to as vehicle headway distance) may be determined by processing an image or series of images captured by the back image capture device 222 to determine the distance of the vehicle 108 from other vehicles on the road in front of the vehicle 108 (block 424). For example, the images captured by the back image capture device 222 may be analyzed to compare the visual area of an object in front of the vehicle in one or more images (i.e., if the visual area is larger in a first image relative to a second image, the object was likely closer at the time the second image was capture whereas if the visual area of the object is smaller in a first image relative to a second image, the object was likely further away at the time the second image was captured) and/or the visual area of the road between the vehicle 108 and an object (i.e., if the visual area of the road is larger in a first image relative to a second image, the object was likely further away at the time the second image was capture whereas if the visual area of the road is smaller in a first image relative to a second image, the object was likely closer away at the time the second image was captured). Additionally or alternatively, if the back image capture device 222 is properly calibrated, a single image of the road ahead of the vehicle may be sufficient to estimate the distance of the vehicle 108 from the vehicle ahead using known trigonometric principles. The mobile device 110 and/or on-board computer 114 may determine vehicle position relative to other vehicles regularly with a timestamp and store the log in data storage 228 or send the log to the server 140 for remote storage. Additionally, information from the GPS unit 206 may be incorporated into the log to add information about the current velocity and/or location of the vehicle 108.

The accelerometer array 224 may be used to monitor forces on the vehicle in the X, Y, and/or Z axis and create accelerometer logs (block 426). In some embodiments, the Y-axis may be oriented along left to right axis of the mobile device 110 and/or on-board computer 114, the Z-axis may be oriented along the top to bottom axis of the mobile device 110 and/or on-board computer 114, and the X-axis may be oriented along the front to back axis of the mobile device 110 and/or on-board computer 114. However, the axes could be oriented in any number of ways. The mobile device 110 and/or on-board computer 114 may determine the magnitude of a force along one of the axes and make an accelerometer log with a timestamp in data storage 228 or send the accelerometer log to the server 140 for remote storage.

Figure 5A:
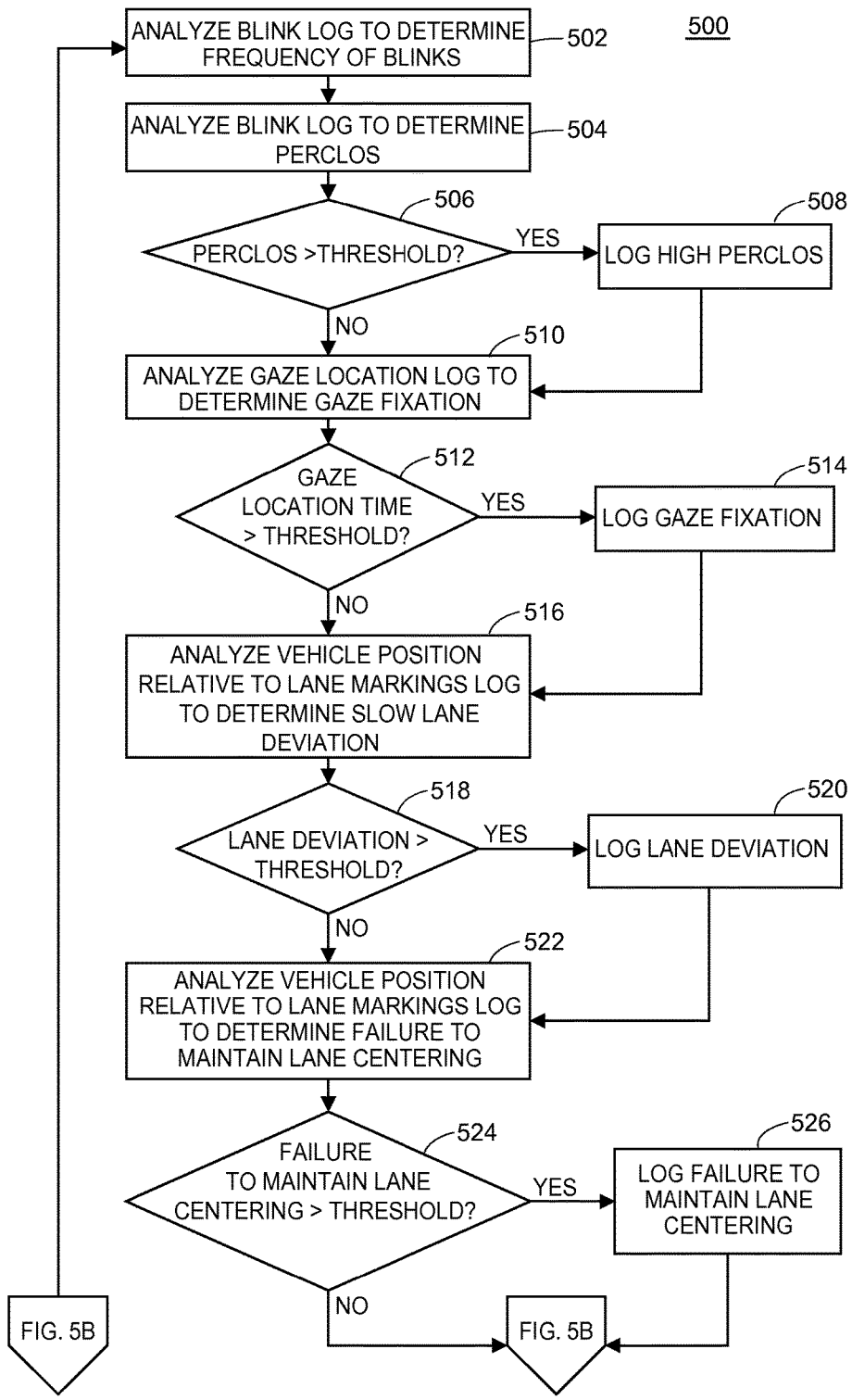
FIGS. 5A-B depict an exemplary secondary impairment indicator logging method for implementing the vehicle operator impairment monitoring system in accordance with the presently described embodiments.
Figure 5B:
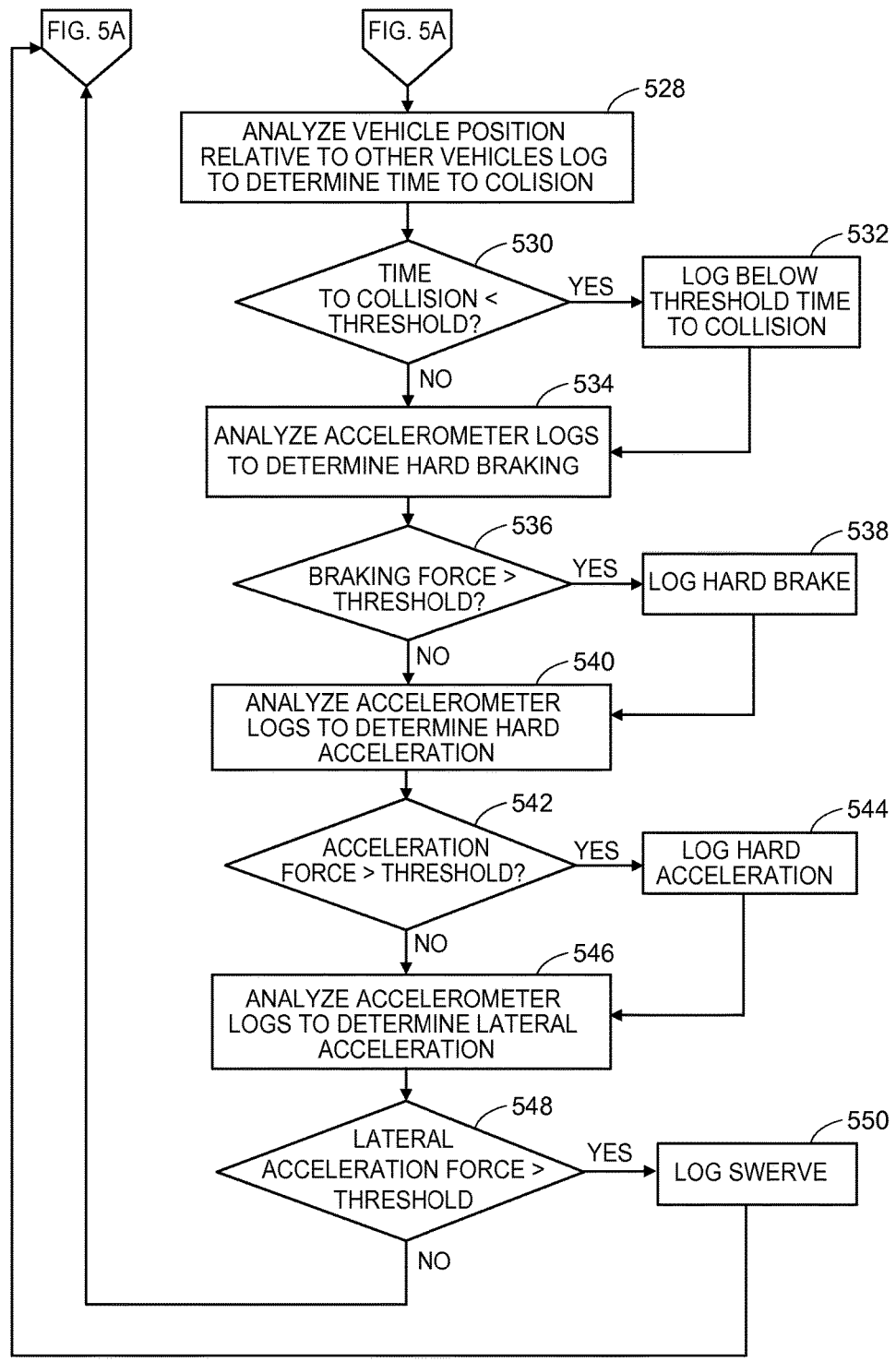

FIGS. 5A-B are flow diagrams depicting an exemplary embodiment of a secondary impairment indicator logging method 500 implemented by the vehicle operator impairment monitoring system 100 while gathering data about potential vehicle operator impairment at block 306. Referring to FIG. 5A, with the log of vehicle operator blinks, the vehicle operator impairment monitoring system 100 may determine the frequency of vehicle operator blinks. Frequency of vehicle operator blinks is a measurement of a function of the time between blinks. For example, a calculation of the frequency of vehicle operator blinks may be made by dividing the total number of blinks in a certain period of time (e.g., 1 min., 2 min. etc.) by the certain time period to calculate the average time between blinks in that time period (block 502). Additionally, with the log of vehicle operator blinks, the vehicle operator impairment monitoring system 100 may determine the percentage of frames the vehicle operator's 106 eyes are closed during a time window (herein after referred to as "PERCLOS") (block 504). PERCLOS may be the sum of the duration of all blinks in a time window divided by the length of the time window. The time window may be of moderate length (e.g., 1 minute, 2 minutes, 5 minutes, etc.). The PERCLOS value may then be compared to a threshold level (e.g., 30%) to determine whether the PERCLOS has exceeded the threshold (block 506). The threshold level may be set during calibration at block 304 (e.g., by measuring the average PERCLOS during calibration as the threshold) and/or configured by a sensitivity setting. If PERCLOS has exceeded the threshold, the client application 232 may make a high PERCLOS log (block 508).

Vehicle operator gaze fixation may be determined by analyzing a set of vehicle operator gaze location logs and determining the length of time in which the vehicle operator 106 is looking at a particular place (block 510). It will be understood that when looking at a particular place, a vehicle operator 106 may move his or her eyes slightly. Such minor variations may be disregarded subject to a sensitivity setting as discussed below. Vehicle operator gaze fixation records instances where a vehicle operator has looked at the same object for more than a threshold period of time (e.g., 100 ms) (block 512). For example, vehicle operator gaze fixation may be used to detect when the vehicle operator 106 has his or her gaze fixed on the road above a threshold level (e.g., the vehicle operator 106 has not looked at mirrors or dashboard in a more than two seconds). Additionally or alternatively, vehicle operator gaze fixation may be determined by analyzing a set of vehicle operator gaze location logs and determining the eye movement of the vehicle operator 106 by calculating the degree to which the vehicle operator's 106 eyes have moved in a first image relative to a second image. When employing such an eye movement velocity-based gaze detection algorithm, vehicle operator gaze fixation may record instances where the velocity of eye movement is below a threshold value (e.g., thirty-five degrees per second). If vehicle operator gaze fixation is detected, the client application 232 may make a gaze fixation log (block 514).

With the logs of vehicle position relative to lane markings, lane deviation may be determined by analyzing the logs of vehicle position relative to lane markings to determine when the distance between a lane marking and vehicle 108 indicates that the vehicle 108 has changed lanes (block 516). While lane changes are a normal aspect of vehicle operation, a slow lane change may indicate that the operator 106 is impaired (e.g., that the driver has fallen asleep or is distracted). Accordingly, the vehicle operator impairment monitoring system 100 may analyze the log of vehicle position relative to lane markings to detect lane changes that occur over a period of time greater than a threshold value (e.g., twenty seconds, thirty seconds, etc.) (block 518). When a slow lane deviation is detected, the client application may make a slow lane deviation log (block 520).

With the logs of vehicle position relative to lane markings, failure to maintain lane centering may be determined by analyzing the logs of vehicle position relative to lane markings to determine when the distance between a lane marking and vehicle 108 indicates that the vehicle 108 is not centered in the lane (block 522). Similarly to lane deviation, if a vehicle 108 starts to veer from the center of the lane over a long period of time, this may indicate that the vehicle operator 106 is impaired. Accordingly, the vehicle operator impairment monitoring system 100 may analyze the log of vehicle position relative to lane markings to detect an increasing failure to maintain lane centering that occurs over a period of time greater than a threshold value (e.g., fifteen seconds) (block 524). The client application 232 may use two threshold values: a first threshold value (e.g., three seconds) to detect distraction and a second threshold to detect drowsiness (e.g., fifteen seconds). When a failure to maintain lane centering is detected, the client application 232 may make a log (block 526). If the client application 232 uses a first and second threshold, the client application 232 may make separate logs for each respective threshold.

With the logs of vehicle position relative to other vehicles, time to collision may be determined by analyzing the logs of vehicle position relative to other vehicles to determine when a decreasing time to collision indicates that the vehicle 108 may be too close behind another vehicle (block 528). Time to collision may be calculated in a number of ways (e.g., by dividing the distance between the vehicle 108 and the vehicle ahead by the difference velocity between the two vehicles, etc.). Next, the client application 232 may determine the visual area of an object in front of the vehicle 108 in a first image, determine the visual area of the object in a second image, and calculate the difference between the two areas. Then, the time to collision may be estimated by noting the change in the difference between the two areas relative to the amount of time between the first time and the second time. Additionally or alternatively, the client application 232 may determine the visual area of the road in front of the vehicle 108 in a first image, determine the visual area of the road in a second image, and calculate the difference between the two areas. Then, the time to collision may be estimated by noting the change in the difference between the two areas relative to the amount of time between the first time and the second time. Alternatively, the distance between the vehicle 108 and the vehicle ahead may be calculated with a single image using trigonometry as discussed above. Input from the GPS unit 206 may be used to determine current velocity of the vehicle 108. The vehicle operator impairment monitoring system 100 may analyze the log of vehicle position relative to other vehicles to detect when time to collision decreases below a threshold value (e.g., 2 second etc.) (block 530). When a below threshold time to collision is detected, the client application 232 may make a time to collision below threshold log (block 532). Alternatively or additionally, the data used to calculate time to collision may also be used to calculate similar metrics such as time to brake (i.e., the amount of time the vehicle operator 106 has to apply the brakes in order to prevent collision with an object) and/or time to react (i.e., the amount of time a vehicle operator 106 has to recognize an imminent collision and react to prevent it by swerving and/or applying the brakes). In addition to the data used to calculate time to collision, it may be advantageous to incorporate additional data into the calculation of time to brake and time to react such as the stopping capability of the vehicle 108, road conditions (e.g., wet, icy, unpaved, etc.), and the reaction time of the vehicle operator 106 (e.g., determined by a test performed on the individual vehicle operator 106, calculated by adjusting average human reaction time to account for the vehicle operator's 106 age, health, impairment level as determined herein, etc.). As with time to collision, time to brake and/or time to react may be compared to a threshold time and used to generate an impairment log.

With the accelerometer logs, vehicle braking or deceleration may be monitored by noting deceleration sensed by an accelerometer oriented in the fore-aft direction of the vehicle (i.e., the X-axis) (block 534). If the force measured by the accelerometer array 224 indicates that the brakes of the vehicle 108 have been applied sharply (e.g., the force measured in the X-axis exceeds a threshold value) (block 536), the client application 232 may make a hard brake log (block 538).

With the accelerometer logs, vehicle acceleration may be monitored by noting acceleration sensed by an accelerometer oriented in the fore-aft direction of the vehicle (i.e., the X-axis) (block 540). If the force measured by the accelerometer array 224 indicates that the accelerator of the vehicle 108 has been applied sharply (e.g., the force measured in the X-axis exceeds a threshold value) (block 542), the client application 232 may make a sharp acceleration log (block 544).

With the accelerometer logs, vehicle lateral acceleration may be monitored by analyzing forces measured by an accelerometer oriented along the left to right side of the vehicle 108 (i.e., the Y-axis) (block). If the force measured by the accelerometer array 224 indicates that the vehicle 108 has swerved (e.g., the force measured in the Y-axis exceeds a threshold value) (block 548), the client application 232 may make a swerve log (block 550).

In embodiments where the mobile device 110 and/or on-board computer 114 is a thin client device, the mobile device 110 and/or on-board computer 114 may send the logs to the server 140 soon after logging the recorded information. In such embodiments, the server 140 may analyze the logs of primary impairment indicators as discussed above to determine secondary impairment indicators.

Figure 6:
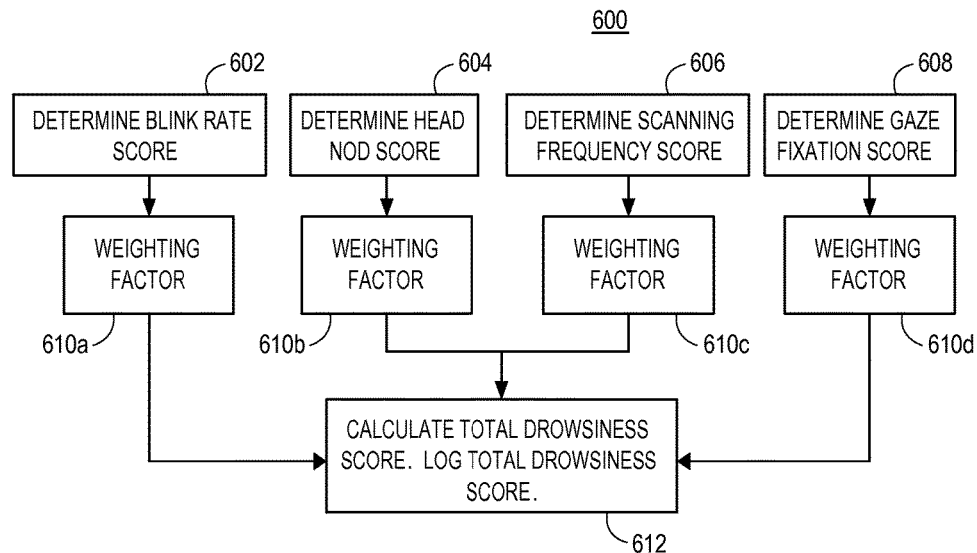
FIG. 6 depicts an exemplary vehicle operator drowsiness score determination method for implementing the vehicle operator impairment monitoring system in accordance with the presently described embodiments.
Figure 7:
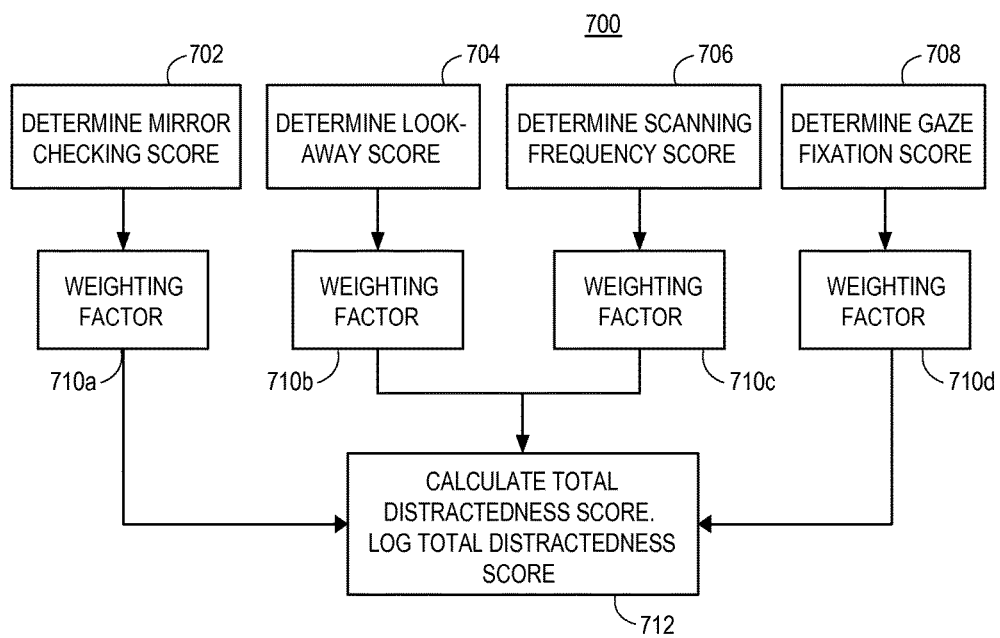
FIG. 7 depicts an exemplary vehicle operator distractedness score determination method for implementing the vehicle operator impairment monitoring system in accordance with the presently described embodiments.

Referring again to FIG. 3, after gathering primary and secondary impairment indicators, the vehicle operator impairment monitoring system 100 may analyze the primary and secondary impairment indicators to determine whether the vehicle operator 106 is impaired (e.g., having trouble staying awake, distracted, etc.) (block 308). Such analysis may be performed by the mobile device 110 and/or on-board computer 114, the server 140, or a combination. Determining whether the vehicle operator 106 is impaired may include separate but complimentary determinations such as whether the driver is drowsy, as shown in FIG. 6, or distracted, as shown in FIG. 7. Of course, it will be appreciated by those of ordinary skill in the art that these determinations may be made with a single process as well.

FIG. 6 is a flow diagram depicting an exemplary embodiment of a vehicle operator drowsiness score determination 600 implemented by the vehicle operator impairment monitoring system 100 while determining whether the vehicle operator 106 is impaired at block 308. The method 600 first determines a blink rate score using one or more impairment indicator logs (block 602). Blink rate score may be determined by subtracting 1 point from a total score of 100 every time the blink rate of the vehicle operator 106 exceeds a threshold value (e.g., three blinks per second) during a certain period of time (e.g., 1 minute, 2 minutes). The method 600 may also determine a head nod score using one or more impairment indicator logs (block 604). Head nod score may be determined by subtracting 1 point from a total score of 100 every time a head nod is detected during a certain period of time. The method 600 may also determine a scanning frequency score using one or more impairment indicator logs (block 606). Scanning frequency score can be determined by subtracting 1 point from a total score of 100 every time the vehicle operator 106 fails to shift his or her gaze from one important area for vehicle operation (e.g., the road, mirrors, etc.) to another important area for vehicle operation within a threshold period of time (e.g., 5 seconds) with a certain period of time. For example, a vehicle operator 106 who is drowsy may not look from the road to check the mirrors and speed indicator with sufficient frequency. The method 600 may also determine a gaze fixation score using one or more impairment indicator logs (block 608). The gaze fixation score may be determined by subtracting 1 point from a total score of 100 every time gaze fixation is detected during a certain period of time. After determining scores for the individual primary and secondary impairment indicators as discussed above, the method 600 may multiply each score by a weighting factor 610$a$, $b$, $c$, $d$. For example, if each score is weighted equally, the weighting factors 610$a$-$d$ may all be 0.25. However, it may be advantageous to weight one score higher than another. For example, head nods may indicate that the vehicle operator 106 is falling asleep and may be more important than scanning frequency or gaze fixation in determining whether the vehicle operator 106 is drowsy. In such an embodiment, the weighting factors 610$a$-$d$ may be 0.25, 35, 20, and 20 respectively. In some embodiments, the weighting factors may be adjusted based on previous data for the user or for a large group of users. The weighting factors may be adjusted by one of the many known learning algorithms such as a support vector machine (SVM) or neural network algorithms. The method 600 may then sum the weighted scores to determine a total drowsiness score (block 612). The total drowsiness score may be logged in with a timestamp and stored in data storage 228 and/or sent to the server 140 for remote storage. Referring again to FIG. 3, if the drowsiness score is below an impairment threshold value (e.g., 90 out of 100), the vehicle operator impairment monitoring system 100 may determine that the vehicle operator 106 is drowsy (block 310). Alternatively, it will be understood that instead of a weighted sum adding up to a total drowsiness score, the client application 232 may instead be a weighted sum that is subtracted from a maximum drowsiness score. In such a case, the individual scores discussed above may be calculated differently (e.g., the blink rate score may be determined by incrementing a counter every time a below threshold value is detected).

FIG. 7 is a flow diagram depicting an exemplary embodiment of a vehicle operator distractedness score determination method 700 implemented by the vehicle operator impairment monitoring system 100 while determining whether the vehicle operator 106 is impaired at block 308. The method 700 may determine a mirror checking score using one or more impairment indicator logs (block 702). A mirror checking score may be determined by subtracting 1 point from a total score of 100 every time the vehicle operator fails to look at a mirror within a threshold period of time over a certain period of time (e.g., 1 minute, 2 minutes). The method 700 may also determine a look-away score using one or more impairment indicator logs (block 704). Look-away score may be determined by subtracting 1 point from a total score of 100 every time the frequency or duration of a look-away exceeds a threshold period of time during a certain period of time. Look-aways include head rotations and when the vehicle operator's 106 gaze location is on a distraction (e.g., the stereo, a mobile phone, etc.). The method 700 may also determine a scanning frequency score using one or more impairment indicator logs (block 706). Scanning frequency score can be determined by subtracting 1 point from a total score of 100 every time the vehicle operator 106 fails to shift his or her gaze from one important area for vehicle operation (e.g., the road, mirrors, etc.) to another important area for vehicle operation within a threshold period of time (e.g., 5 seconds) within a certain period of time. For example, a vehicle operator 106 who is distracted may not look from the road to check the mirrors and speed indicator with sufficient frequency. The method 700 may also determine a gaze fixation score using one or more impairment indicator logs (block 708). The gaze fixation score may be determined by subtracting 1 point from a total score of 100 every time gaze fixation is detected during a certain period of time. After determining scores for the individual primary and secondary impairment indicators as discussed above, the method 700 may multiply each score by a weighting factor 710a, b, c, d similar to the weighting factors for the vehicle operator drowsiness detection method 600 discussed above. The weighting factors may be adjusted by one of the many known learning algorithms such as a SVM. The method 700 may then sum the weighted scores to determine a total distractedness score (block 712). The total distractedness score may be logged in with a timestamp and stored in data storage 228 and/or sent to the server 140 for remote storage. Referring again to FIG. 3, if the distractedness score is below an impairment threshold value (e.g., 90 out of 100), the vehicle operator impairment monitoring system 100 may determine that the vehicle operator 106 is distracted (block 310). Alternatively, it will be understood that instead of a weighted sum adding up to a total distractedness score, the client application 232 may instead be a weighted sum that is subtracted from a maximum drowsiness score. In such a case, the individual scores discussed above may be calculated differently (e.g., the gaze fixation score may be determined by incrementing a counter every time a below threshold value is detected).

While FIGS. 6 and 7 describe embodiments of methods 600 and 700 using weighted sums to determine total drowsiness or distractedness scores, respectively, other mathematical operations may be used to determine the total drowsiness or distractedness scores. While the exemplary embodiment discussed above uses a 100 point scale, it will be appreciated that a 100 point scale is just one of many point scales that could be used (e.g., 50 point scale, 200 point scale, 500 point scale, 1000 point scale, etc.). Additional primary and secondary indicators may be used in the determination of the drowsiness score and/or distractedness scores. For example, slow lane deviation, failure to maintain lane centering, below threshold time to collision, hard brake, sharp acceleration, and/or swerve impairment indicators may be added to the calculation of the drowsiness and/or distractedness scores. Each of the slow lane deviation, failure to maintain lane centering, below threshold time to collision, hard brake, sharp acceleration, and/or swerve impairment indicators may be used to generate a respective score similar to the scores described in connection to FIGS. 6 and 7. For example, a respective score for each may be calculated by subtracting 1 point from a total score of 100 for every instance of a slow lane deviation, failure to maintain lane centering, below threshold time to collision, hard brake, sharp acceleration, or swerve, respectively. Once a score for some or all of the slow lane deviation, failure to maintain lane centering, below threshold time to collision, hard brake, sharp acceleration, and/or swerve impairment has been calculated, scores may be added to the weighted sum discussed above. It will be appreciated that when additional scores are added to the weighted sum, it may be advantageous to change the weighting coefficient for some or all of the other scores in the weighted sum.

Figures 12, 13:
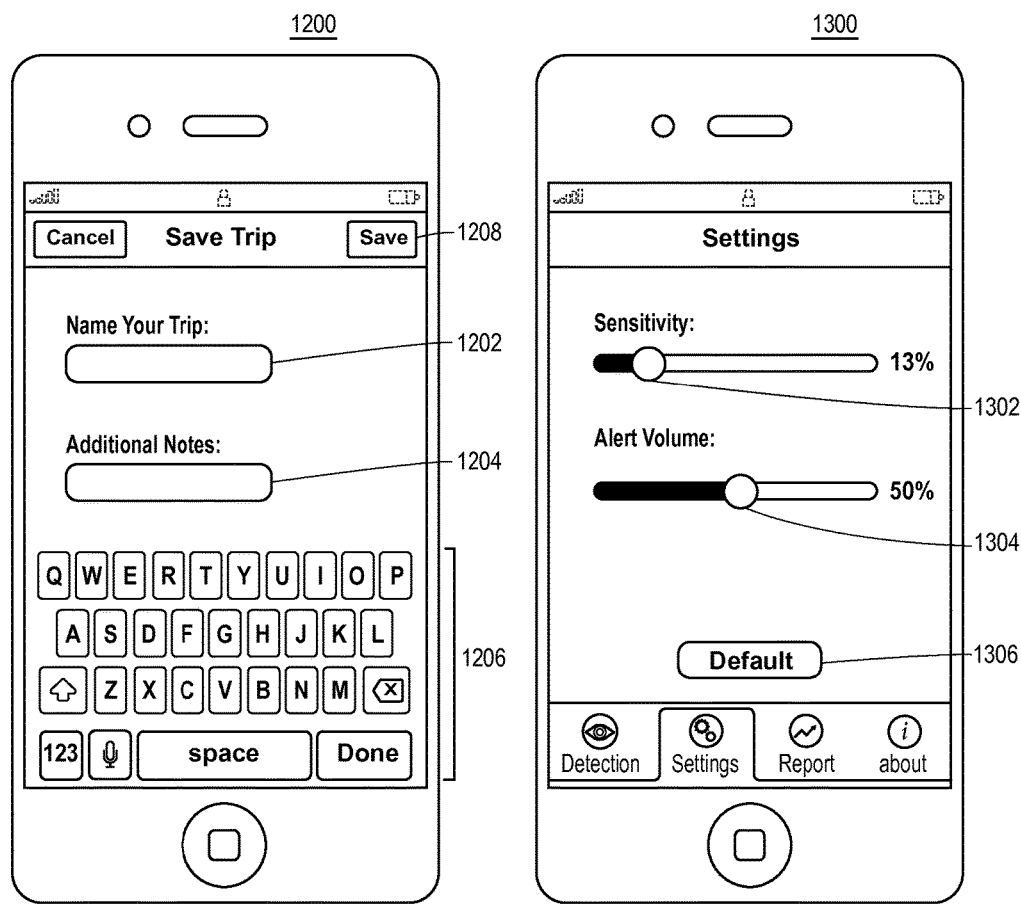

The vehicle operator impairment monitoring system 100 may permit the user to adjust the sensitivity setting for either or both of the drowsiness or distractedness scores. For example, the user may be able to adjust a global setting (e.g., a value between 1 and 100) which may increase or decrease the sensitivity of the vehicle operator impairment monitoring system 100, as shown in FIG. 13. The lowest sensitivity may be represented by the "1" setting and the highest sensitivity may be represented by the "100" setting. The sensitivity setting may raise or lower the impairment threshold value, may be used to generate a coefficient by which the total drowsiness and/or distractedness scores may be multiplied (e.g., "1" could cause the total drowsiness score to be multiplied by 1.3, "100" could cause the total drowsiness score to be multiplied by "0.9"), and/or may be used to generate a value to add to the total drowsiness and/or distracted (e.g., "1" could cause a value of 20 to be added to the total drowsiness score, "100" could cause a value of −20 to be added to the total drowsiness score). Additionally or alternatively, the vehicle operator impairment monitoring system 100 may include one of the many known learning algorithms such as a SVM to adjust the individual threshold values discussed in connection with FIGS. 6 and 7 (e.g., the blink rate threshold of three blinks per second). The learning algorithm may operate in connection with the server 140 to adjust the individual threshold level based on calculations performed using aggregated data from some or all of the mobile devices 110 and/or on-board computers 114 in the vehicle operator impairment monitoring system 100.

Referring again to FIG. 3, when the vehicle operator impairment monitoring system 100 has determined that the vehicle operator 106 is impaired, the vehicle operator impairment monitoring system 100 may alert the vehicle operator 106 using audio, visual alerts, and/or tactile alerts (block 312). Audible alerts may include chime, claxon, siren, etc. and/or a custom recorded sound such as a sound clip or ringtone. Visual alerts may include displaying icons on the display 202, displaying flashing icons on the display 202, and/or activating one or more lights (not shown) coupled to the mobile device 110 and/or on-board computer 114. Tactile alerts may include a tactile alert system 110 vibrating, poking, or otherwise tactilely notifying the vehicle operator 106. In embodiments where the mobile device 110 and/or on-board computer 114 is a thin-client device, the server 140 may send a command to the thin-client device to activate the audible, visual, and/or tactile alerts. In addition to the vehicle operator 106, it may be advantageous to alert other people such as passengers in the vehicle 108. Such passengers may be able to ameliorate the impairment of the vehicle operator 106 (e.g., by talking to the vehicle operator 106 to keep him or her awake, etc.) or be prompted to assume control of the vehicle 106. Further, it may be advantageous to alert authorized third parties outside the vehicle 108, such as a parent/guardian of the vehicle operator 106, the owner of the vehicle 108, the employer of the vehicle operator 108, a law enforcement agency or other first responders, etc. The owner of the vehicle 108 and/or holder of the property and casualty insurance policy covering the vehicle 108, for example, may authorize third parties.

Figure 10:
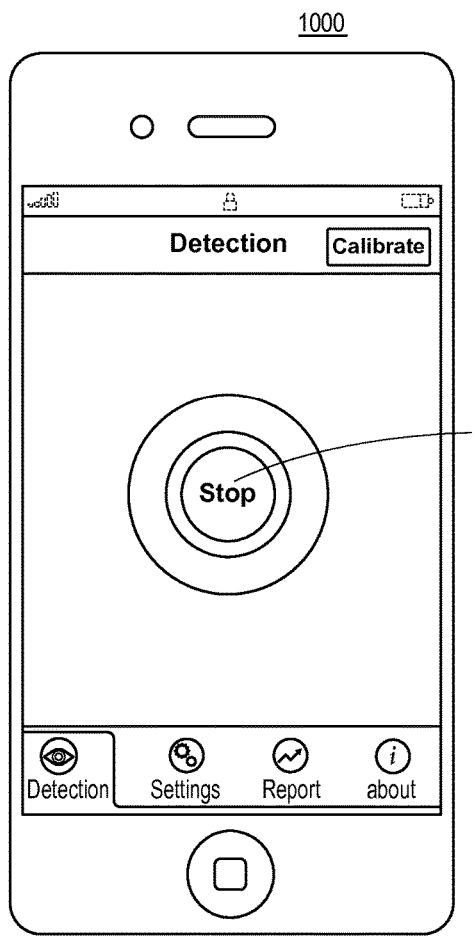

The vehicle operator impairment monitoring system 100 may continue to gather and analyze data while a particular trip is ongoing (block 314). The trip may become completed by a user command (e.g., the user selects a "Stop" button as shown in FIG. 10) and/or automatically (e.g., the mobile device 110 and/or on-board computer 114 detects that the engine of the vehicle 108 has stopped). When the trip is complete, the vehicle operator impairment monitoring system 100 may analyze the data collected during the just completed trip along with data from previous trips to provide metrics and suggestions to the user. For example, the vehicle operator impairment monitoring system 100 may analyze the impairment score(s) of a user with the time and date of each trip to determine patterns in the user's impairment. For example, the vehicle operator impairment monitoring system 100 may analyze thirty trips over the course of two weeks and determine that the user tends to be most impaired around the hours of 12 P.M. and 6 P.M. Accordingly, the vehicle operator impairment monitoring system 100 may recommend that the user avoid driving around the hours of 12 P.M. and 6 P.M. or take other ameliorative action(s) (e.g., drinking a caffeinated beverage shortly before operating the vehicle at high impairment times, removing distractions by turning off the stereo at high impairment times).

FIGS. 8-14 depict client application pages or screens that may be displayed on the display 202 of the mobile device 110 as part of the user interface used to implement the vehicle operator impairment monitoring system 100. While FIGS. 8-14 depict client application pages or screens being displayed on the display 202 of the mobile device 110, it will be understood that the client application pages or screens could be displayed on the display 202 of the on-board computer 114 in addition to being displayed on the mobile device 110 or as an alternative. The client applications or pages may be generated by the mobile device 110 or sent to the mobile device 110 by the server 140 (e.g., as with a thin client). The user may launch the client application 232 from the mobile device 110 via any suitable manner, such as touch-selecting a client application icon (not shown) on the display 202 of the mobile device 110 or speaking a voice command into the microphone (not shown) of the mobile device 110. After the user launches the client application 232, the client application 232 may begin to run on the mobile device 110 at described above in connection to block 302.

Figure 8:
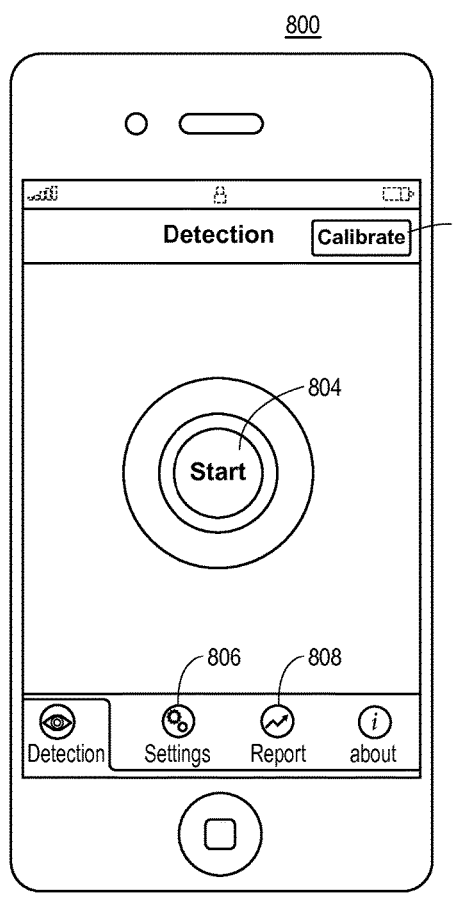
FIGS. 8-14 depict embodiments user interface screens associated with a client application with the present description.

With reference now to FIG. 8, a home screen 800 of the client application 232 may be displayed on the display 202 of the mobile device 110. The home screen 800 may include a "Calibrate" button 802, a "Start" button 804, a "Settings" tab 806, and a "Report" tab 808. When the user selects the calibrate button 802 the client application 232 may execute a calibration routine at described above in connection to block 304.

Figure 9:
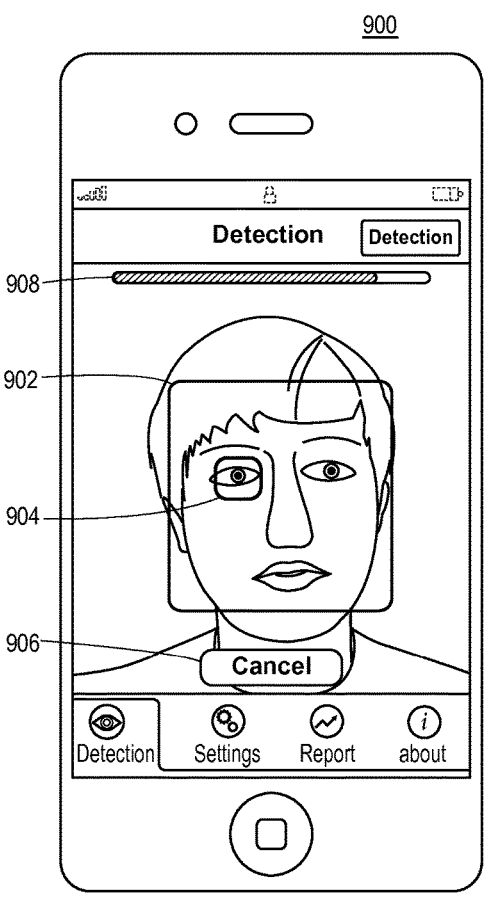

With reference now to FIG. 9, a calibration screen 900 of the client application 232 may be displayed on the display 202 of the mobile device 110 during a calibration routine executed in connection to block 304. The calibration screen 900 may include a face detection indicator 902, eye detection indicator 904, the "Cancel" button 906, and a calibration progress indicator 908. While the client application 232 is executing the calibration routine discussed in connection to block 304, the calibration screen 900 may display a face detection indicator 902 showing on the display 202 the visual area perceived by the client application 232 to be the face of the user 106 and/or an eye detection indicator 904 showing on the display the visual area perceived by the client application 232 to be an eye of the user 106. If a user selects the cancel button 906, calibration may be terminated. A calibration progress indicator 908 may display an approximate indication of the status of the calibration routine.

Referring again to FIG. 8 when the user selects the "Start" button 804, the client application 232 may begin to collect data about potential vehicle operator impairment, analyze the data, and/or alert the vehicle operator 106 if impairment is detected (blocks 306-314). With reference now to FIG. 10, vehicle operator impairment detection screen 1000 may be displayed on the display 202 of the mobile device 110 executed in connection with blocks 306-314. The vehicle operator impairment detection screen 1000 may include a "Stop" button 1002. If the "Stop" button 1002 is selected by the user, the vehicle operator impairment monitoring system 100 may terminate operator impairment monitoring. Selecting the "Stop" button 1002 may also permit the user to save additional information about the trip as well as launch a save trip screen 1200 as shown in FIG. 12.

Figure 11:
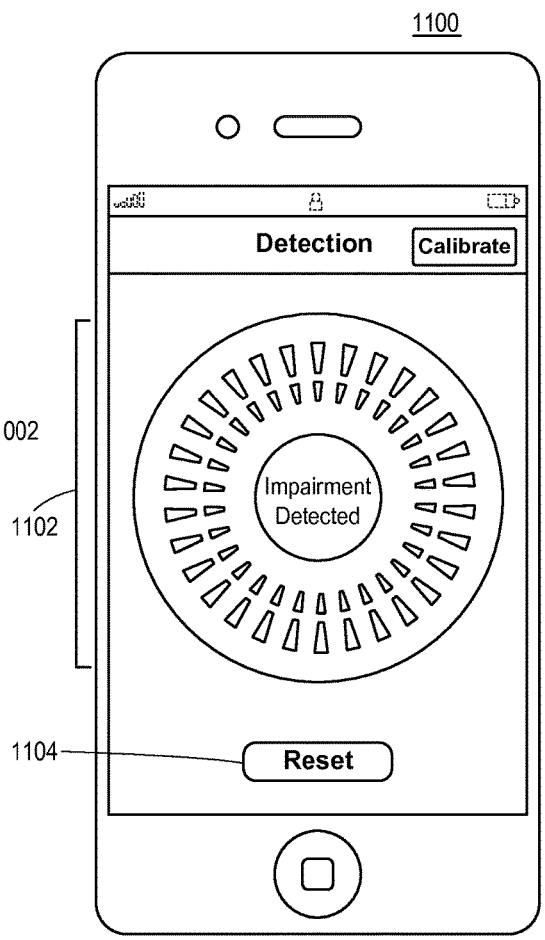

With reference now to FIG. 11, an impairment detected alert screen 1100 of the client application 232 may be displayed on the display 202 of the mobile device 110 executed in connection to block 312. The impairment detected alert screen 1100 may include a visual alert 1102 and a "Reset" button 1104. The visual alert 1102 may include a visual icon, motion, and/or flashing icons. If the "Reset" button 1104 is selected by the user, the vehicle operator impairment monitoring system 100 may clear the impairment detected alert screen 1100 and may also restart operator impairment monitoring. While the impairment detected alert screen 1100 is being displayed on the display 202 of the mobile device 110, audible and/or tactile alerts may also be generated as discussed above.

With reference now to FIG. 12, a save trip screen 1200 of the client application 232 may be displayed on the display 202 of the mobile device 110 used in connection with block 316. The save trip screen 1200 may include a trip name entry field 1202, an additional notes entry field 1204, an on-screen keyboard 1206, and a "Save" button 1208. A user may input a name of the trip into the trip name entry field 1202 and/or the additional notes entry field 1204 using the on-screen keyboard at 1206, a physical keyboard (not shown), and/or voice input. Selecting the "Save" button 1208 may cause the data from the trip (e.g., impairment indicators, individual impairment indicators scores, total impairment score, etc.) to be saved in data storage 228 and/or to be sent to the server 140 for remote storage.

Referring again to FIG. 8 when the user selects the settings tab 806, a settings screen 1300 may be displayed on the display 202 of the mobile device 110 as shown in FIG. 13. The settings screen 1300 may include a sensitivity adjustment control 1302, an alert volume adjustment control 1304, and a "Default" button 1306. Adjusting the sensitivity adjustment control 1302 (e.g., by sliding a virtual slider) may increase or decrease the sensitivity setting of the vehicle operator impairment monitoring system 100 as discussed above. The alert volume adjustment control 1304 may be used to increase or decrease (e.g., by sliding a virtual slider) the volume of audio, visual, and/or tactile alerts. The "Default" button 1306 may be used to set the sensitivity adjustment control 1302 and alert volume adjustment control 1304 back to their default settings.

Figure 14:
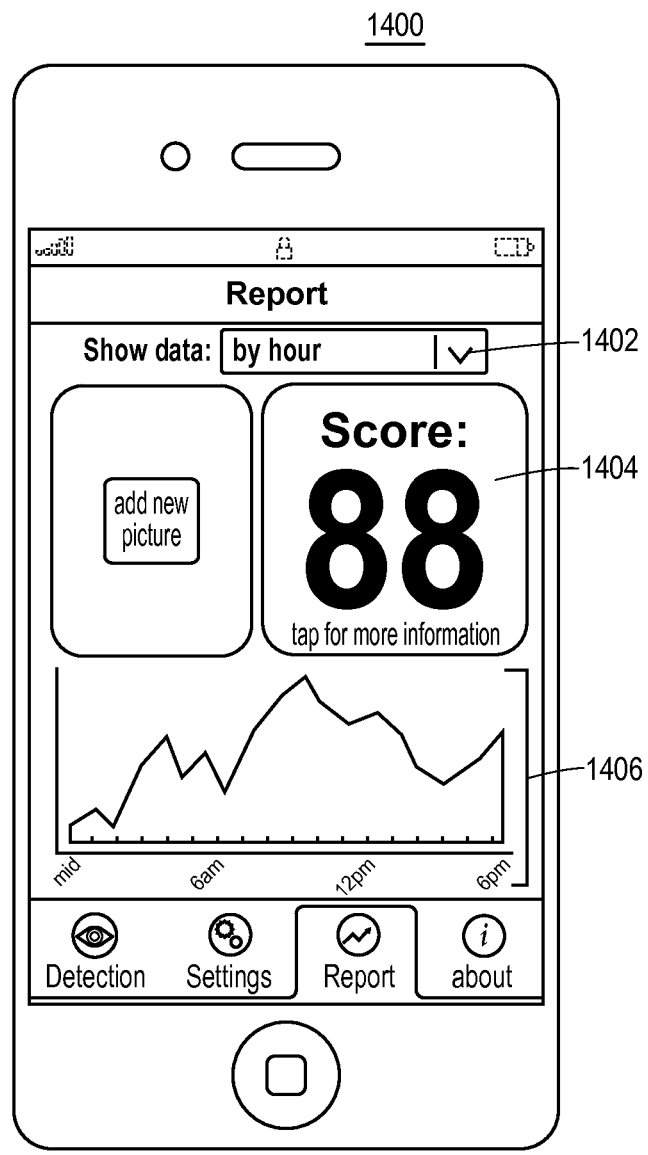

Referring again to FIG. 8, when the user selects the report tab 808, a report screen 1400 may be displayed on the display 202 of the mobile device 110 as shown in FIG. 14 used in connection with block 316. The report screen 1400 may include a data range adjustment control 1402, an average total impairment score 1404, and a graph of time versus total impairment scores 1406. The data range adjustment control 1402 may be used to change the time axis (i.e., the X-axis) of the graph of time versus total impairment scores 1406 (e.g., show data by hour, by day, by month, by year, etc.). The average total impairment score 1404 may display the average total impairment score of the most recently completed trip or an average of all of the trips for which the vehicle operator impairment monitoring system 100 has data.

Figure 15:
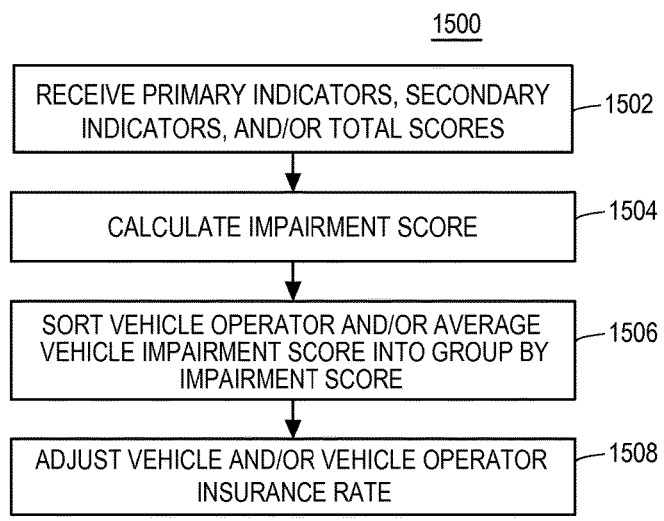
FIG. 15 depicts an insurance rate adjustments method for implementing the vehicle operator impairment monitoring system in accordance with the presently described embodiments.

FIG. 15 is a flow diagram depicting an exemplary embodiment of an insurance rate adjustments method 1500 implemented by the vehicle operator impairment monitoring system 100. More particularly the method 1500 may be performed by the server 140. The server 140 may receive some or all of the data collected or generated by the mobile device 110 and/or onboard computer 114 relating to the primary indicators, secondary indicators, primary indicators scores, secondary indicators scores, total drowsiness score, and/or total distracted score discussed above over the network 130 (block 1502). The server 140 may then determine one or more scores based on the data received to block 1502 (block 1504). For example, the server 140 may determine a total impairment score representing a summary of the vehicle operator's 106 level of impairment.

Figure 16:
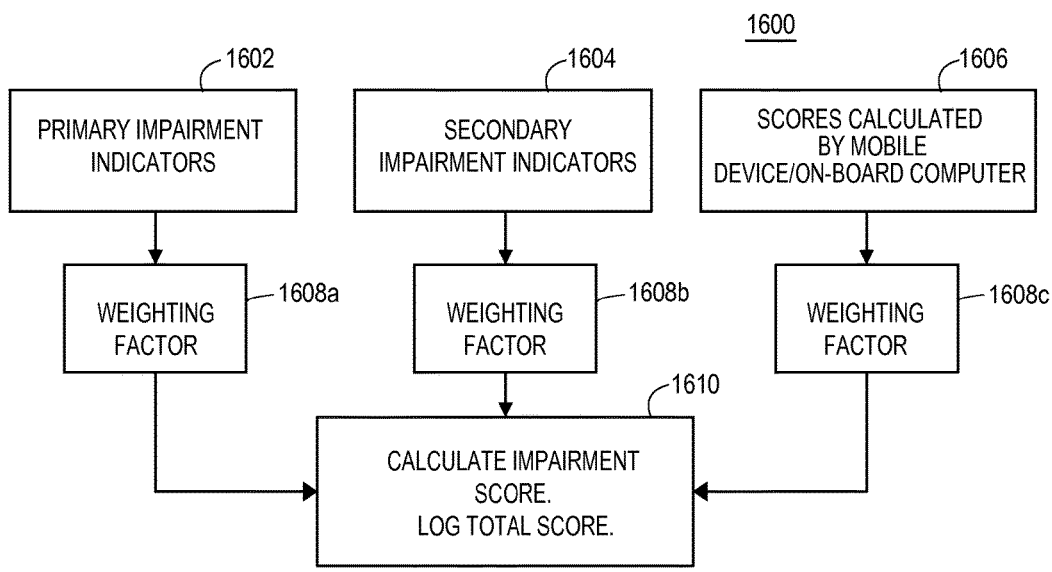
FIG. 16 depicts an exemplary total impairment score determination method for implementing the vehicle operator impairment monitoring system in accordance with the presently described embodiments.

FIG. 16 is a flow diagram depicting an exemplary embodiment of a total impairment score determination method 1600 implemented by the vehicle operator impairment monitoring system 100 while determining a total impairment score for the vehicle operator 106 at block 1504. The method 1600 may receive primary indicators from the mobile device 110 and/or onboard computer 114 (block 1602), secondary indicators from the mobile device 110 and/or onboard computer 114 (block 1604), and/or scores calculated by the mobile device 110 and/or onboard computer 114 (block 1606). If the method 1600 receives primary and/or secondary indicators, the server 140 may generate scores for each primary and/or secondary indicator in a manner similar to how the mobile device 110 and/or onboard computer 114 calculates scores as discussed above. For example, the server 140 may determine a mirror checking score using primary and/or secondary indicators, determine a scanning frequency score using primary and/or secondary indicators, etc. Because the memory and computing power of the server 140 may be greater than the mobile device and/or onboard computer 114, it may be advantageous to calculate the various scores using a longer period of time (e.g., an average mirror checking score over one week rather than over a number of minutes). The server 140 may also receive impairment scores and/or total drowsiness and/or total distractedness scores from the mobile device 110 and/or onboard computer 114. In a manner similar to FIGS. 7 and 8, the method 1600 may determine a total impairment score by multiplying each score by a weighting factor 1608a, b, c. Each score may be weighted equally. However, it may be advantageous to weight one score higher than another. The method 1600 may then sum the weighted scores to determine a total impairment score (block 1610). The total impairment score may be logged in with a timestamp and stored.

Referring again to FIG. 15, once the total impairment score has been calculated, the total impairment score may be used to sort the property and casualty insurance policy of the vehicle and/or vehicle operator and/or vehicle owner into an impairment level group with the policies of other vehicle operators with similar total impairment scores (block 1506). The impairment level groups may be set to follow a normal distribution, however the impairment level groups may also be set to follow other known distribution models. The number of impairment level groups may be any of a number of numbers (e.g., ten impairment level groups) and the groups may or may not be evenly distributed along the normal curve. Each of the groups may have an insurance policy rate increase or decrease amount. For example, if there are ten impairment level groups where Impairment Level Group 1 includes policies of vehicle operators associated that have the highest impairment scores (indicating a high level of impairment) and Impairment Group 10 includes policies that have the lowest impairment scores, then policies grouped in Impairment Level Groups 1-3 may be associated with an insurance rate increase (e.g., 15%, 10%, and 5%, respectively), Impairment Level Groups 4-6 may not be associated with an increase or decrease, and Impairment Level Groups 7-10 may be associated with an insurance rate decrease (e.g., −5%, −10%, and −15%, respectively). Further, it may be advantageous to flag policies with particularly high levels of impairment for cancellation of the insurance policy. In some embodiments, the policies grouped in the most impaired groups may not be charged an increased rate. In such embodiments, the prospect of a discount without the risk of an insurance rate increase may be used to entice a vehicle operator 106 to use the vehicle operator impairment monitoring system 100. Once the property and casualty insurance policy of the vehicle and/or vehicle operator and/or vehicle owner has been sorted into the appropriate group, the discount or increase that may be associated with the group may be applied to the policy of the vehicle operator 106 (block 1508). More than one vehicle operators 106 may be on the same policy (e.g., a married couple, a family with children on the policy, etc.). If more than one vehicle operator 106 is on the same policy, the vehicle operator impairment monitoring system 100 may be used to adjust the rate for the entire policy based on the individual impairment scores of the various vehicle operators 106. Additionally or alternatively, the individual impairment scores may be aggregated and/or averaged to adjust the rate for the entire policy.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

We claim:

1. A mobile device of a vehicle operator, the mobile device comprising:
   a display;
   one or more sensors, including a first camera and a second camera;

a processor; and a memory storing instructions that, when executed by the processor, cause the mobile device to present to the vehicle operator, on the display, a user interface with at least one sensitivity adjustment control, the at least one sensitivity adjustment control being adjustable by the vehicle operator to control sensitivity of impairment monitoring, detect a sensitivity setting of the at least one sensitivity adjustment control, the sensitivity setting resulting from an adjustment of the sensitivity adjustment control by the vehicle operator via the user interface, generate first impairment log entries by (i) monitoring the vehicle operator with the first camera while the vehicle operator operates a vehicle, (ii) determining whether each of one or more characteristics of the vehicle operator exceed a respective threshold, and (iii) generating an impairment log entry for each instance in which one of the one or more characteristics exceeds its respective threshold, generate second impairment log entries by monitoring an environment ahead of the vehicle with the second camera, determine a total impairment score for the vehicle operator, at least by (i) assigning a plurality of scores based on the first impairment log entries and the second impairment log entries, and (ii) performing a mathematical operation on the plurality of scores, determine whether the total impairment score exceeds a score threshold, wherein one or both of (i) determining the total impairment score, and (ii) determining whether the total impairment score exceeds the score threshold, is based on the sensitivity setting, in response to determining that the total impairment score exceeds the score threshold, present an alert to the vehicle operator.

2. The mobile device of claim 1, wherein:

the one or more sensors further include one or more accelerometers; and the instructions cause the mobile device to generate third impairment log entries by monitoring force in one or more directions with the one or more accelerometers, and assign the plurality of scores based on the first impairment log entries, the second impairment log entries, and the third impairment log entries.

3. The mobile device of claim 1, wherein:

the first impairment log entries are primary impairment log entries;

the instructions cause the mobile device to (i) generate secondary impairment log entries based on the primary impairment log entries, and (ii) assign the plurality of scores based in part on the secondary impairment log entries.

4. The mobile device of claim 3, wherein:

the primary impairment log entries include entries corresponding to instances of eye blinks by the vehicle operator; and the secondary impairment log entries include at least one entry corresponding to a frequency of eye blinks by the vehicle operator.

5. The mobile device of claim 4, wherein the instructions cause the mobile device to generate the at least one entry corresponding to the frequency of eye blinks in response to determining that the frequency exceeds a threshold corresponding to the sensitivity setting.

6. The mobile device of claim 3, wherein:

the primary impairment log entries include entries corresponding to gaze locations of the vehicle operator; and the secondary impairment log entries include at least one entry corresponding to gaze fixation by the vehicle operator.

7. The mobile device of claim 6, wherein the instructions cause the mobile device to generate the at least one entry corresponding to gaze fixation in response to determining that a duration of the gaze fixation exceeds a threshold corresponding to the sensitivity setting.

8. The mobile device of claim 1, wherein:

the second impairment log entries are primary impairment log entries; and the instructions cause the mobile device to (i) generate secondary impairment log entries based on the primary impairment log entries, and (ii) assign the plurality of scores based in part on the secondary impairment log entries.

9. The mobile device of claim 1, wherein the instructions cause the mobile device to present the alert to the vehicle operator by one or more of:

showing, on the display, an alert icon;

generating, via a speaker of the mobile device, an audible alert; or generating a tactile alert.

10. A mobile device of a vehicle operator, the mobile device comprising:

a display;

one or more sensors, including a first camera and a second camera;

a processor; and a memory storing instructions that, when executed by the processor, cause the mobile device to present to the vehicle operator, on the display, a user interface with at least one sensitivity adjustment control, the at least one sensitivity adjustment control being adjustable by the vehicle operator to control sensitivity of impairment monitoring, detect a sensitivity setting of the at least one sensitivity adjustment control, the sensitivity setting resulting from an adjustment of the sensitivity adjustment control by the vehicle operator via the user interface, generate first impairment log entries by (i) monitoring the vehicle operator with the first camera while the vehicle operator operates a vehicle, (ii) determining whether each of one or more characteristics of the vehicle operator exceed a respective threshold, wherein the respective threshold corresponds to the sensitivity setting, and (iii) generating an impairment log entry for each instance in which one of the one or more characteristics exceeds its respective threshold, generate second impairment log entries by monitoring an environment ahead of the vehicle with the second camera, send the first impairment log entries and the second impairment log entries to a server for remote processing, in response to sending the first impairment log entries and the second impairment log entries, receive, from the server, an alert indication, and in response to receiving the alert indication, present an alert to the vehicle operator.

11. The mobile device of claim 10, wherein:

the one or more sensors further include one or more accelerometers; and the instructions cause the mobile device to
generate third impairment log entries by monitoring force in one or more directions with the one or more accelerometers,
send the third impairment log entries to the server for remote processing, and
receive the alert indication in response to sending the first impairment log entries, the second impairment log entries, and the third impairment log entries.

12. The mobile device of claim 10, wherein:
the first impairment log entries are primary impairment log entries;
the instructions cause the mobile device to (i) generate secondary impairment log entries based on the primary impairment log entries, and (ii) send the secondary impairment log entries to the server; and
the alert indication is received also in response to sending the secondary impairment log entries to the server.

13. The mobile device of claim 12, wherein:
the primary impairment log entries include entries corresponding to instances of eye blinks by the vehicle operator; and
the secondary impairment log entries include at least one entry corresponding to a frequency of eye blinks by the vehicle operator.

14. The mobile device of claim 13, wherein the instructions cause the mobile device to generate the at least one entry corresponding to the frequency of eye blinks in response to determining that the frequency exceeds a threshold corresponding to the sensitivity setting.

15. The mobile device of claim 12, wherein:
the primary impairment log entries include entries corresponding to gaze locations of the vehicle operator; and
the secondary impairment log entries include at least one entry corresponding to gaze fixation by the vehicle operator.

16. The mobile device of claim 15, wherein the instructions cause the mobile device to generate the at least one entry corresponding to gaze fixation in response to determining that a duration of the gaze fixation exceeds a threshold corresponding to the sensitivity setting.

17. The mobile device of claim 10, wherein:
the second impairment log entries are primary impairment log entries; and
the instructions cause the mobile device to (i) generate secondary impairment log entries based on the primary impairment log entries, and (ii) send the secondary impairment log entries to the server; and
the alert indication is received also in response to sending the secondary impairment log entries to the server.

18. The mobile device of claim 17, wherein:
the primary impairment log entries include entries corresponding to lane deviations by the vehicle; and
the secondary impairment log entries include at least one entry corresponding to a lane change by the vehicle.

19. The mobile device of claim 18, wherein the instructions cause the mobile device to generate the at least one entry corresponding to a lane change in response to determining that a duration of the lane change exceeds a threshold corresponding to the sensitivity setting.

20. The mobile device of claim 10, wherein the instructions cause the mobile device to present the alert to the vehicle operator by one or more of:
showing, on the display, an alert icon;
generating, via a speaker of the mobile device, an audible alert; or
generating a tactile alert.

* * * * *